(12) United States Patent
Fukae et al.

(10) Patent No.: US 8,822,752 B2
(45) Date of Patent: Sep. 2, 2014

(54) DISPOSABLE DIAPER

(75) Inventors: Akinori Fukae, Shikokuchuo (JP);
Masahiro Kaneda, Shikokuchuo (JP);
Akiko Jinno, Shikokuchuo (JP);
Sachiko Ono, Shikokuchuo (JP)

(73) Assignee: Diao Paper Corporation, Ehime (JP)

( * ) Notice: Subject to any disclaimer, the term of this patent is extended or adjusted under 35 U.S.C. 154(b) by 628 days.

(21) Appl. No.: 13/002,173

(22) PCT Filed: Jun. 30, 2009

(86) PCT No.: PCT/JP2009/061963
§ 371 (c)(1),
(2), (4) Date: Dec. 30, 2010

(87) PCT Pub. No.: WO2010/001893
PCT Pub. Date: Jan. 7, 2010

(65) Prior Publication Data
US 2011/0112496 A1    May 12, 2011

(30) Foreign Application Priority Data

Jun. 30, 2008 (JP) ................. 2008-171654
Jun. 30, 2008 (JP) ................. 2008-171655
Nov. 28, 2008 (JP) ................. 2008-304049
Nov. 28, 2008 (JP) ................. 2008-304050

(51) Int. Cl.
*A61F 13/15* (2006.01)
*A61F 13/551* (2006.01)
*A61F 13/51* (2006.01)

(52) U.S. Cl.
CPC ..... *A61F 13/5512* (2013.01); *A61F 2013/5109* (2013.01)
USPC ..................... 604/359; 604/385.13

(58) Field of Classification Search
CPC ............ A61F 13/551; A61F 13/51484; A61F 13/5512; A61F 2013/55125; A61F 2013/55155; A61F 2013/8408; A61F 2013/5109; A61F 2013/51076
USPC .............................. 604/359, 385.13
See application file for complete search history.

(56) References Cited

U.S. PATENT DOCUMENTS 4,654,256 A * 3/1987 Doree et al. ............... 428/304.4
4,775,585 A * 10/1988 Hagiwara et al. ............. 428/323

(Continued)

FOREIGN PATENT DOCUMENTS

JP    58-179119     11/1983
JP    02-080050 A   3/1990

(Continued)

OTHER PUBLICATIONS

Machine Translation of Japanese Patent Abstract for 58-179119, published on Nov. 30, 1983.

*Primary Examiner* — Lynne Anderson
*Assistant Examiner* — Peter S Vasat
(74) *Attorney, Agent, or Firm* — Renner Kenner; Arthur M. Reginelli

(57) ABSTRACT

[Problem] To provide a disposable diaper more effective in odor eliminating.
[Means for Solving Problem] The above problem is solved by a disposable diaper, comprising a liquid pervious face sheet 30, a liquid impervious sheet 11, an absorbent body 56 interposed therebetween, an outer sheet 12 covering a back surface of the liquid impervious sheet 11, an after-treatment tape on an external surface of a back body part B and an odor eliminating printed sheet 25 interposed between the liquid impervious sheet 11 and the outer sheet 12 in the body part B having the after-treatment tape and formed by printing with ink a sheet base material.

19 Claims, 21 Drawing Sheets

(56) References Cited

U.S. PATENT DOCUMENTS

| | | |
|---|---|---|
| 6,653,521 B1 | 11/2003 | Kurata |
| 2002/0177836 A1* | 11/2002 | Hayase et al. ............ 604/385.13 |
| 2004/0122386 A1* | 6/2004 | Mocadlo ........................ 604/359 |
| 2004/0122387 A1* | 6/2004 | Long et al. .................... 604/360 |
| 2004/0127866 A1* | 7/2004 | Odorzynski ................... 604/359 |
| 2007/0026209 A1* | 2/2007 | MacDonald et al. ......... 428/207 |
| 2008/0033381 A1* | 2/2008 | Albino et al. ................. 604/358 |
| 2008/0103470 A1 | 5/2008 | Samuelsson |

FOREIGN PATENT DOCUMENTS

| | | |
|---|---|---|
| JP | 06-245954 A | 6/1994 |
| JP | 09-253125 | 9/1997 |
| JP | 10-130592 A | 5/1998 |
| JP | 3061324 | 2/1999 |
| JP | 11-076296 A | 3/1999 |
| JP | 11-104171 A | 4/1999 |
| JP | 11-192261 A | 7/1999 |
| JP | 11-192673 A | 7/1999 |
| JP | 2000-350745 A | 12/2000 |
| JP | 2001-046423 A | 2/2001 |
| JP | 2003-024377 | 1/2003 |
| JP | 2005-131382 | 5/2005 |
| JP | 2008-138300 A | 6/2008 |
| JP | 2008-161249 | 7/2008 |
| WO | WO 2006/135017 A1 | 6/2006 |

\* cited by examiner

DISPOSABLE DIAPER

TECHNICAL FIELD

The present invention relates to disposable diapers.

BACKGROUND ART

In general, a disposable diaper after use is rolled or folded such that a surface thereof with excretion is positioned inside, and is placed into a highly airtight storage container such as a sanitary box or a diaper storage container for temporary storage, and then is moved into a garbage bag for disposal when a certain quantity of diapers have been stored within the container. Disposable diapers after use smell a strong excretion odor and cause a user a discomfort feeling. Therefore, there have been suggested several techniques for suppressing an excretion odor from disposable diapers after use, such as arranging a deodorant sheet containing zeolite on the inside of a top sheet (Patent Document 1) and configuring a crepe paper sheet covering an absorbent body to contain a deodorant (Patent Document 2), and others.

CITATION LIST

Patent Documents

Patent Document 1: JP 2001-046423 A
Patent Document 2: JP 2000-350745 A

DISCLOSURE OF THE INVENTION

Technical Problem to be Solved

However, the foregoing related arts have a problem of being less effective in eliminating an odor from a diaper after use, considering an used amount of a deodorant.

Accordingly, a main object of the present invention is to provide a disposable diaper more effective in odor eliminating.

Means to Solve the Problems

The present invention to solve the foregoing problem is as follows:
<Invention According to Claim 1>
A disposable diaper, comprising a liquid pervious face sheet, a liquid impervious sheet, an absorbent body interposed between the two sheets, and an odor eliminating printed sheet arranged on the liquid impervious sheet on an opposite side of the absorbent body,
the disposable diaper having a back body part extending backward from a center of the diaper in a longitudinal direction, a front body part extending frontward from the center of the diaper in the longitudinal direction, and an after-treatment tape on an external surface of at least one of the front body part and the back body part to fix the diaper in a state of being rolled or folded with the face sheet positioned inside, wherein the odor eliminating printed sheet is arranged on at least one of the front body part and the back body part whichever has the after-treatment tape, and is smaller in area than the body part on which the same is arranged, and at least part of the same overlaps the absorbent body.
(Effect and Operation)
Among various absorbent articles, a disposable diaper in particular is commonly configured to be rolled or folded after use such that the face sheet is positioned inside and the body part having the after-treatment tape is positioned outside, and then be fixed in that state for disposal. In such a disposal mode, the diaper emits an odor of excretion attached to the face sheet and absorbed by the absorbent body to the outside through the body part having the after-treatment tape. Accordingly, when the odor eliminating printed sheet and the after-treatment tape of the present invention are arranged in a positional relationship as described above, the odor eliminating printed sheet is located in a main path of the odor in the disposal mode of the rolled or folded diaper, thereby performing odor elimination in a more effective manner. In addition, the odor eliminating printed sheet is located nearer to the outside in the disposal mode of the rolled or folded diaper, thereby exerting also an odor eliminating effect on an odor on the outside of the diaper such as an odor within the storage container, for example. Further, in the foregoing configuration, odor elimination can be achieved effectively without having to provide the odor eliminating printed sheet on the entire external surface of the diaper, which results in high cost performance.
<Invention According to Claim 2>
The disposable diaper according to Claim 1, wherein
the odor eliminating printed sheet is provided with a design print, and the design print can be seen from an external surface side of the diaper.
(Effect and Operation)
It is conventional practice to arrange a printed sheet only with a design print (not containing a deodorant particle) so as to be visible from the external surface side of the diaper. Accordingly, it is preferred to provide the odor eliminating printed sheet with a design print so as to also serve as a design printed sheet.
<Invention According to Claim 3>
The disposable diaper according to Claim 2, wherein
the odor eliminating printed sheet is an air permeable sheet containing nonwoven fabric or paper as base materials, and
the odor eliminating printed sheet is arranged on both the front body part and the back body part, and the after-treatment tape is arranged on at least one of the front body part and the back body part.
(Effect and Operation)
If the odor eliminating printed sheet is to also serve as a design printed sheet, it is preferred to arrange the odor eliminating printed sheet both on the front body part and the back body part, so as to increase a design area and raise the degree of freedom of a position for arrangement of the after-treatment tape.
In addition, when a sheet base material for the odor eliminating printed sheet is an air permeable sheet, the sheet base material itself exerts somewhat of an odor eliminating effect by odor absorption, and increases a probability of contact between an odor and the deodorant due to a large surface area and air permeability thereof. Accordingly, the sheet base material preferably has such characteristics for improvement of odor eliminating efficiency.
<Invention According to Claim 4>
The disposable diaper according to Claim 3, wherein
the after-treatment tape has a base portion fixed to the external surface of the diaper and an engage portion that is positioned nearer to a tip portion than the base portion and is engaged on the external surface of the diaper, and
the after-treatment tape is arranged in such a manner that at least part of the base portion overlaps the odor eliminating printed sheet in the body part on which the same is arranged.
(Effect and Operation)
The after-treatment tape is generally arranged only at a central portion of the back body part in a lateral direction. In this case, when the after-treatment tape is positioned such that at least part of the base portion overlaps the odor eliminating printed sheet in the body part on which the same is arranged, the odor eliminating printed sheet can be located in a more preferred position in the disposal mode of the rolled or folded diaper.

<Invention According to Claim 5>

The disposable diaper according to Claim 4, wherein the odor eliminating printed sheet has an area of 30% or more of an area of the absorbent body in the body part on which the same is arranged, and overlaps the absorbent body by 80% or more of the area, and the liquid impervious sheet has a moisture permeability of 6,000 g/m$^2$·24 h or more.

(Effect and Operation)

The odor eliminating printed sheet is preferably arranged with such an area and at such a position as described above, in terms of an odor eliminating effect.

In addition, when the liquid impervious sheet is high in moisture permeability as stated above, the diaper is comfortable for a wearer due to efficient discharge of moisture, but is also prone to emit an odor. In the present invention, however, the liquid impervious sheet lets efficiently an odor pass through to contact the odor eliminating printed sheet, and therefore it is rather preferred to enhance the liquid impervious sheet in moisture permeability. The moisture permeability here refers to a value measured by JIS K 7129 (A method).

<Invention According to Claim 6>

The disposable diaper according to Claim 5, wherein the after-treatment tape has a tab part at a tip portion thereof and has a transparent or translucent part other than the tab part, and the printed design can be seen from the external surface side through the transparent or translucent remaining part of the after-treatment tape.

(Effect and Operation)

If the base portion of the after-treatment tape is to overlap the odor eliminating printed sheet with the design print, when the after-treatment tape is entirely opaque, the after-treatment tape may hide partially the design print of the odor eliminating printed sheet. Accordingly, the after-treatment tape is preferably made transparent or translucent except for the tab part, so that the printed design can be seen from the external surface side through the transparent or translucent part of the after-treatment tape.

<Invention According to Claim 7>

The disposable diaper according to Claim 6, comprising an outer sheet made from nonwoven fabric to cover a back surface of the liquid impervious sheet, the odor eliminating printed sheet being interposed between the liquid impervious sheet and the outer sheet, wherein the odor eliminating printed sheet and the liquid impervious sheet are stuck to each other by an attachment area of 70% or less of an area of the odor eliminating printed sheet, and the odor eliminating printed sheet and the outer sheet are stuck to each other by an attachment area of 80% or more of the area of the odor eliminating printed sheet.

(Effect and Operation)

If the odor eliminating printed sheet and the after-treatment tape of the present invention are to be arranged in a positional relationship as described above, when the attachment area between the odor eliminating printed sheet and the adjacent sheet is set as described above, it is possible to form a larger space with lower air permeability on the outside of the diaper between the odor eliminating printed sheet and the liquid impervious sheet positioned on the absorbent body side. This allows an odor from the liquid impervious sheet side to efficiently contact the printed sheet, thereby enhancing an odor eliminating effect.

<Invention According to Claim 8>

The disposable diaper according to Claim 4, wherein the after-treatment tape is arranged on a left side of a left edge of the absorbent body and on a right side of a right edge of the same, and the odor eliminating printed sheet is arranged in such a manner that a line linking the right and left after-treatment tapes straddles the odor eliminating printed sheet.

(Effect and Operation)

The after-treatment tapes may be arranged on both sides of right and left edges as a mode of arrangement of the same. Even in this case, when the after-treatment tapes are configured such that a line linking the right and left after-treatment tapes straddles the odor eliminating printed sheet as described above, the odor eliminating printed sheet can be located in a more preferred position in the disposal mode of the rolled or folded diaper.

<Invention According to Claim 9>

The disposable diaper according to Claim 4, wherein the odor eliminating printed sheet has a sheet base material and a deodorant particle fixed to the sheet base material with an adhesive resin, and part of the deodorant particle on an outer surface is not covered with the adhesive resin.

(Effect and Operation)

As described above, when positioned on a back surface side of the liquid impervious sheet, the deodorant particle has a significant odor eliminating effect in particular during storage of the diaper after use. In addition, if a resin is used as an attachment means (ink, an adhesive, or the like as described later) to fix the deodorant particle to the back surface side of the liquid impervious sheet, the deodorant particle does not function sufficiently when the entire surface of the deodorant particle is covered with the resin. However, if part of the outer surface of the deodorant particle is not covered with the adhesive resin as described above, the deodorant particle functions with reliability.

<Invention According to Claim 10>

The disposable diaper according to Claim 9, wherein the deodorant particle has an average particle diameter of 2.0 to 8.0 μm, the deodorant particle accounts for 50 to 100 parts by weight with respect to 100 parts by weight of the adhesive resin, and a total content of the deodorant particle and the adhesive resin is 0.10 to 0.60 g per 1 m$^2$ of the odor eliminating printed sheet.

(Effect and Operation)

When the adhesive resin containing the deodorant particle with such an average particle diameter and such a density is used with such a basis weight, it is possible to preferably expose most of the deodorant particle on a coating film of the adhesive resin. An excessively small amount of the deodorant agent produces a poor odor eliminating effect, whereas an excessively large amount of the deodorant agent makes it difficult to fix the deodorant particle. The average particle diameter here refers to a median size defined by JIS K 1474-2007.

<Invention According to Claim 11>

The disposable diaper according to Claim 10, wherein the adhesive resin is a urethane-based resin.

(Effect and Operation)

Urethane-based resin is preferred as the foregoing adhesive resin in terms of high air permeability.

<Invention According to Claim 12>

The disposable diaper according to Claim 11, wherein the deodorant particle has a three-dimensional structure, a layered structure, or a porous structure, for physical absorption of an odor, and contains a metal ion for chemical absorption of an odor molecule.

(Effect and Operation)

When the deodorant particle absorbing physically an odor becomes wet with a liquid, the inside of the particle structure is filled with the liquid and cannot absorb an odor molecule. Accordingly, if the deodorant particle is arranged in a transfer pathway for a liquid content of excretion and an absorbing/retaining part for the same, the particle becomes less effective in odor eliminating after use of the diaper, considering a used amount of the deodorant particle. Meanwhile, when the deodorant particle is positioned on the back surface side of the liquid impervious sheet as described above, fine pores of the deodorant particle are not filled with a liquid content of excretion, and therefore the deodorant particle exerts a sufficient odor eliminating effect even after use of the diaper. In addition, the deodorant particle has preferably a degradation ability of a metal ion as described above.

<Invention According to Claim 13>

The disposable diaper according to Claim 4, wherein a porous deodorant particle absorbing physically an odor is attached with ink as an attachment means to the sheet base material of the odor eliminating printed sheet.

(Effect and Operation)

When the porous deodorant particle absorbing physically an odor becomes wet with a liquid, fine pores of the same are filled with the liquid and cannot absorb an odor molecule. Accordingly, even if the deodorant particle is arranged in a transfer pathway for a liquid content of excretion and an absorbing/retaining part for the same as in a conventional manner, the particle becomes less effective in odor eliminating after use of the diaper, considering a used amount of the deodorant particle. Meanwhile, when the deodorant particle is positioned on the back surface side of the liquid impervious sheet as described above, fine pores of the deodorant particle are not filled with a liquid content of excretion, and therefore the deodorant particle exerts a sufficient odor eliminating effect even after use of the diaper. In addition, even if any ink solvent or the like enters the fine pores of the deodorant particle, the fine pores are restored (activated) after drying of the ink, and the odor eliminating effect of the deodorant particle is hardly reduced under the influence of the ink. This configuration has another advantage that the diaper can be easily manufactured using existing production facilities, as will be understood from a manufacturing method described later.

<Invention According to Claim 14>

The disposable diaper according to Claim 13, wherein the deodorant particle has an average particle diameter of 0.1 to 10 μm, and the odor eliminating printed sheet has a content of the deodorant particle of 0.01 $g/m^2$ or more per unit area in a part including the deodorant particle.

(Effect and Operation)

It is preferred that the odor eliminating printed sheet contains sufficiently densely the deodorant particle with this average diameter. The average particle diameter here refers to a median size defined by JIS K 1474-2007.

<Invention According to Claim 15>

The disposable diaper according to Claim 14, wherein the sheet base material is provided with a deodorant print with ink containing the porous deodorant particle on a side surface of the liquid impervious sheet, and the sheet base material is provided with a design print on a side surface of the outer sheet.

(Effect and Operation)

It is preferred to provide the design print to the side surface of the outer sheet for improvement of visibility of the design. It is also preferred to provide the print with ink containing the porous deodorant particle to the side surface of the liquid impervious sheet, so that an odor from the liquid impervious sheet side contacts efficiently the deodorant particle. By providing the prints in such a manner, it is possible to prevent interference between the print with ink containing the porous deodorant particle and the design print which deteriorates the diaper in odor eliminating effect and design expressivity.

<Invention According to Claim 16>

The disposable diaper according to Claim 15, wherein the odor eliminating printed sheet is attached intermittently to the liquid impervious sheet, and an attachment area of the same is 70% or less of an area of the odor eliminating printed sheet.

(Effect and Operation)

When the odor eliminating printed sheet and the liquid impervious sheet positioned on the absorbent body side are sparsely attached to each other so as to form spaces between the two sheets, it is possible to allow an odor from the liquid impervious sheet side to contact efficiently the odor eliminating printed sheet, thereby enhancing an odor eliminating effect.

<Invention According to Claim 17>

The disposable diaper according to Claim 13, wherein the deodorant particle is a zeolite particle formed by substituting some or all of an ion-exchangeable ion in zeolite with silver ion, and at least one of the following arrangements (a) to (c) is employed:

(a) a content of silver ion per unit area of the odor eliminating printed sheet is 0.3 $mg/m^2$;

(b) yellow ink is used as the attachment means; and (c) the sheet base material has a total light transmission rate of 50% or less defined by JIS K7105, and has the porous deodorant particle attached only to a side surface of the liquid impervious sheet.

(Effect and Operation)

If the deodorant particle contains a silver ion, the deodorant particle is further effective in odor eliminating because the deodorant particle can absorb an odor physically and chemically. In this case, however, the odor eliminating printed sheet may turn yellow at a part containing the deodorant particle by the action of humidity, sunlight, fluorescence, Nox, and the like. Accordingly, employing the configuration (a) can preferably reduce the degree of discoloration, and employing the configurations (b) and (c) can preferably make the discoloration less noticeable.

<Invention According to Claim 18>

The disposable diaper according to Claim 4, wherein the outer sheet is provided with a perforation on an entire or partial peripheral edge of a covering portion overlapping at least part of a portion of the odor eliminating printed sheet with an odor eliminating function, and the odor eliminating printed sheet is exposed to the outside by cutting out the outer sheet along the perforation and turning up the covering portion.

(Effect and Operation)

As described above, the disposable diaper after use is rolled or folded with a surface with excretion positioned inside, and is placed into a highly air tight storage container for temporary storage, and then is moved into a garbage bag for disposal when a certain quantity of diapers have been stored within the container. In this case, since the used absorbent articles remain in the storage container for a certain period of time (at least an interval between garbage collection days, for example, one or two days, in Japan where absorbent articles fall within the category of combustible garbage), the storage container is completely filled with a foul odor which may cause a user a strong discomfort feeling. Nevertheless, the foregoing prior art has a poor odor eliminating effect on an odor released from the used absorbent articles and filling the storage container.

Meanwhile, if the diaper is configured to expose the odor eliminating printed sheet to the outside as described above by cutting out the outer sheet along the perforation and turning up the covering portion at least partially overlapping the portion of the odor eliminating printed sheet with an odor eliminating effect, when the diaper with the exposed odor eliminating printed sheet is placed into the storage container, the odor eliminating printed sheet contacts directly the odor filling the storage container, thereby achieving odor elimination more effectively.

<Invention According to Claim 19>

The disposable diaper according to Claim 18, wherein the perforation is formed in such a manner that a partial peripheral edge of the covering portion is remained as a continuous part from the outside and the other part of the covering portion is cut out in a zigzag or spiral pattern, and the after-treatment tape is arranged at a tip portion of the cutting part.

(Effect and Operation)

When the perforation for exposing the odor eliminating printed sheet is structured as described above, it is possible to not only expose the odor eliminating printed sheet to the outside, but also fix the article in the rolled or folded state by winding a long part of the outer sheet formed by cutting along the perforation around the rolled or folded article after use and then fastening the long part with the after-treatment tape. Therefore, it is possible to fix the rolled or folded article for disposal while exposing the odor eliminating printed sheet to the outside without having to arrange a long after-treatment tape as in a conventional manner. This allows easy disposal of the used article.

The disposable diaper according to embodiments of the present invention, wherein the perforation includes a first perforation formed in such a manner that a waist side end of the peripheral edge of the covering portion is remained as a continuous part from a waist side part of the same and that the other part of the covering portion is cut and raised as a first cut and rise part; and a second perforation formed in such a manner that a crotch side end of the covering portion within the first cut and rise part is remained as a continuous part from a crotch side part of the same and that a waist side part of the first cut and rise part is cut and raised as a second cut and rise part, and the after-treatment tape is arranged at the second cut and rise part.

(Effect and Operation)

If the perforation for exposing the odor eliminating printed sheet is structured as described above, when the article is cut out along the first and second perforations and the first and second cut and rise parts are raised, it is possible to not only expose the odor eliminating printed sheet to the outside, but also fix the article in the rolled or folded state by winding a long part constituted by the first cut and rise part extending from the outer sheet 12 and the second cut and rise part extending from the first cut and rise part around the rolled or folded article after use and then fastening the long part with the after-treatment tape. Therefore, it is possible to fix the rolled or folded article for disposal while exposing the odor eliminating printed sheet to the outside without having to arrange a long after-treatment tape as in a conventional manner. This allows easy disposal of the used article.

Effect of the Invention

According to the present invention as described above, there are advantages of achieving more effective odor elimination and so on.

BEST MODE FOR CARRYING OUT THE INVENTION

Embodiments of the present invention will be described below in detail with reference to the attached drawings.

FIGS. 1 to 10 show an example of an underpants type disposable diaper. The underpants type disposable diaper includes an outer sheet 12 constituting an external surface (back surface) of the article and an inner body 200 attached to an internal surface of the outer sheet. The inner body 200 is intended to absorb and retain excretion such as urine and the like, and the outer sheet 12 is intended to be attached to the body of a wearer. In the cross section views, dotted portions depict joint portions for constitutional members. Those joint portions are formed by solid, bead, curtain, summit, or spiral application of a hot-melt adhesive or the like. In the following description, the term "longitudinal direction" refers to a direction that links a ventral side (front side) to a back side (rear side); the term "lateral direction" refers to a direction (right-left direction) orthogonal to the longitudinal direction; and the term "up-down direction" refers to a direction that becomes orthogonal to a trunk surrounding direction when the diaper is being used, that is, when the diaper is folded in two such that a front body part and a back body part are overlapped on both sides, in other words, a direction that links a waist opening WO and a crotch portion.

(Inner Body)

Figure 3:
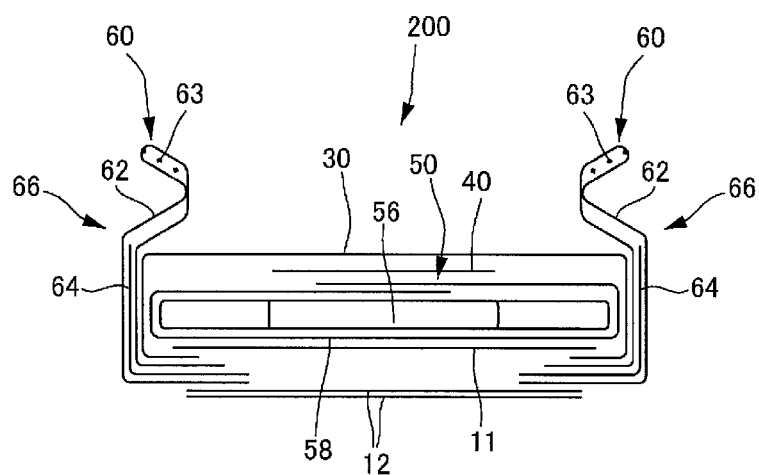
FIG. 3 is a cross-section view of FIG. 1 taken along 3-3.
Figure 4:
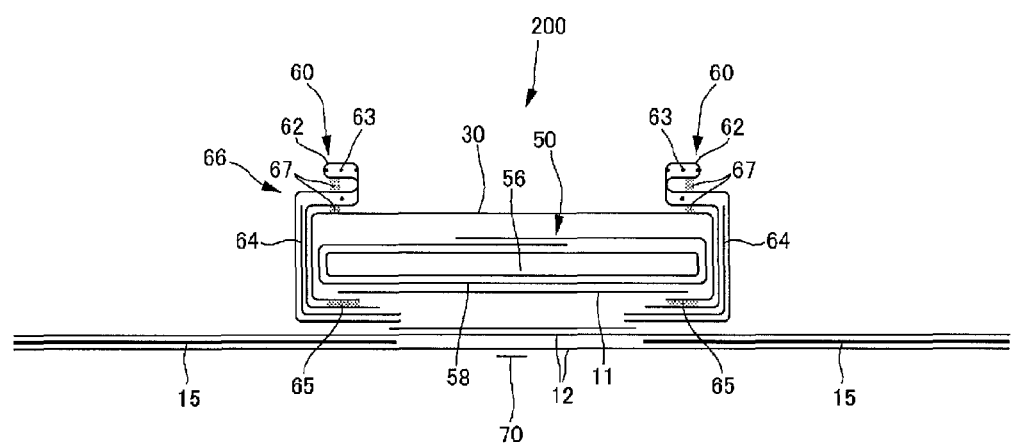
FIG. 4 is a cross-section view of FIG. 1 taken along 4-4.
Figure 5:
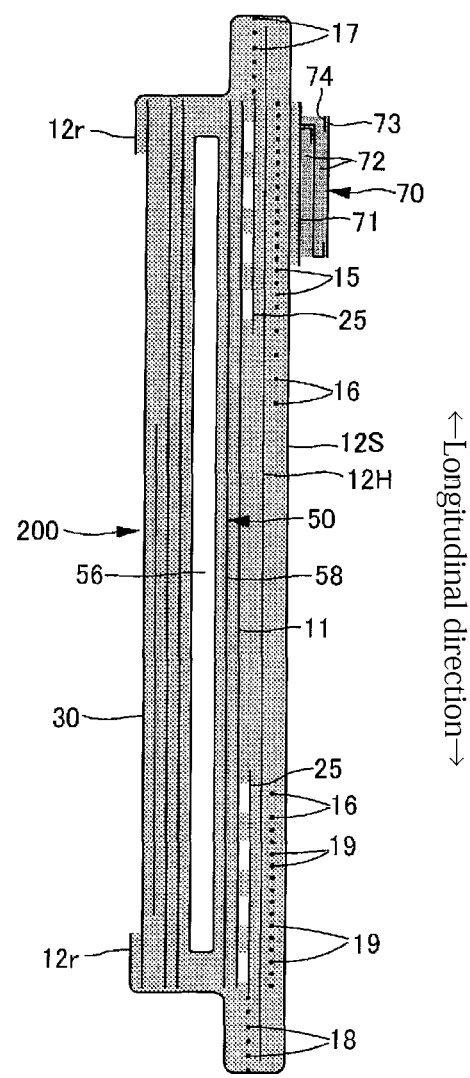
FIG. 5 is a cross-section view of FIG. 1 taken along 5-5.
Figure 6:
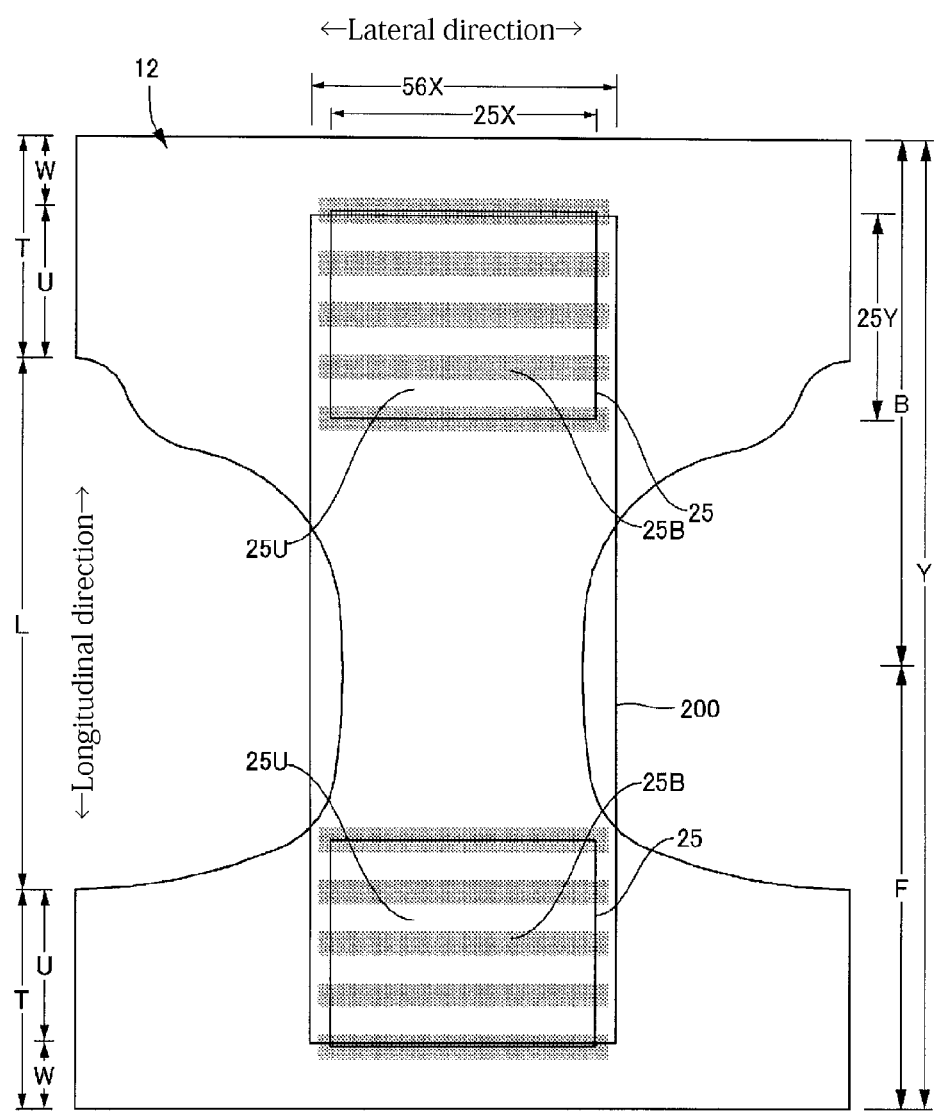
FIG. 6 is a plane view of the opened underpants type disposable diaper, showing major components of the diaper.

The inner body 200 may have any shape, and is of a rectangle in the illustrated arrangement. As shown in FIGS. 3 to 5, the inner body 200 includes a face sheet 30 facing the body of a wearer, a liquid impervious sheet 11, and an absorbent element 50 interposed between the two sheets, and performs a function of liquid absorption. Reference numeral 40 denotes an interlayer sheet (second sheet) interposed between the face sheet 30 and the absorbent element 50 to transfer a liquid having passed through the face sheet 30 quickly to the absorbent element 50. Reference numeral 60 denotes barrier cuffs 60 standing toward the body of a wearer on the both sides of the inner body 200.

(Face Sheet)

The face sheet 30 has a liquid pervious property. Therefore, a material for the face sheet 30 may be a porous or nonporous nonwoven fabric or a porous plastic sheet, for example. In addition, there is no particular limitation on raw fibers for use in such a nonwoven fabric. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, thermal bonding method, melt-blown method, needle punching method, air-through method, point bonding method, and the like. For example, if flexibility and drape property are needed, the spun bonding method and the spun lace method are preferred. If high bulk and softness are required, the air-through method, the point bonding method, and the thermal bonding method are preferred.

In addition, the face sheet 30 may be a single sheet or a laminated sheet obtained by sticking two or more sheets to each other. Similarly, the face sheet 30 may be a single sheet or two or more sheets in a planar direction.

When the barrier cuffs 60 are arranged, it is preferred to extend the both side portions of the face sheet 30 to the underside of the absorbent element through 50 between the liquid impervious sheet 11 and the barrier cuffs 60, and attach the same to the liquid impervious sheet 11 and the barrier cuffs 60 with a hot-melt adhesive or the like in order to prevent liquid permeation.

(Interlayer Sheet)

To rapidly move a liquid having passed through the face sheet 30 to the absorber, it is possible to provide the interlayer sheet 40 (also called "second sheet"), which is higher in liquid permeability rate than the face sheet 30. The interlayer sheet 40 allows a liquid to move quickly to the absorbent body to thereby enhance an absorption performance of the absorbent body. In addition, the interlayer sheet 40 also prevents a "backflow" phenomenon in which a liquid flows back from the absorbent body, thereby to keep a surface of the face sheet 30 in a dry condition. The interlayer sheet 40 may not be provided.

The interlayer sheet 40 may use the same material as that for the face sheet 30, or may use spun lace nonwoven fabric, spun bond nonwoven fabric, SMS nonwoven fabric, pulp nonwoven fabric, a mixed sheet of pulp and rayon, point-bonded or crepe paper, for example. In particular, an air-through nonwoven fabric is high-bulk and thus preferred. Such an air-through nonwoven fabric preferably uses composite fibers of a core-sheath structure. In this case, material resin for the core may be polypropylene (PP) but is preferably high-stiffness polyester (PET). A basis weight of the nonwoven fabric is preferably 20 to 80 g/m$^2$, more preferably 25 to 60 g/m$^2$. A fineness of material fibers for the nonwoven fabric is preferably 2.2 to 10 dtex. To make the nonwoven fabric high-bulk, some or all of the material fibers use preferably mixed fibers with off-center cores or hollow centers, or mixed fibers with off-center cores and hollow centers.

In the illustrated embodiment, the interlayer sheet 40 is made shorter in width than the absorbent body 56 and is centered with respect to the absorbent body 56. Alternatively, the interlayer sheet 40 may be provided across a full width of the absorbent body 56. A length of the interlayer sheet 40 in the longitudinal direction may be the same as that of the absorbent body 56, or may be in a shorter range centered in an area for receiving a liquid.

(Liquid Impervious Sheet)

There is no particular limitation on a material for the liquid impervious sheet 11. For example, the material may be a plastic film made of an olefin resin such as polyethylene or polypropylene, a laminated nonwoven fabric in which a plastic film is provided on a surface thereof, and a layered sheet in which a nonwoven fabric or the like is layered and joined on a plastic film. It is preferred for the liquid impervious sheet 11 to employ a liquid impervious, moisture pervious material that has been favorably used in recent years from the viewpoint of prevention of stuffiness. Widely used as a moisture pervious plastic film is a microporous plastic film obtained by mixing and kneading an inorganic filling agent into an olefin resin such as polyethylene or polypropylene to thereby form a sheet and then extending the sheet in a uniaxial or biaxial direction. Further, the liquid impervious sheet 11 may use a sheet given liquid imperviousness without a plastic film, by using a nonwoven fabric of micro denier fibers, applying heat or pressure to make gaps in fibers smaller with enhanced leakage resistance, coating with a high water-absorption resin or hydrophobic resin, or applying a water repellent agent.

The liquid impervious sheet 11 preferably extends from the both sides of the absorbent element 50 to both sides of a surface of the face sheet 30 side of the absorbent element 50, for enhancement of a leakage prevention property. The extended portion has an appropriate width of about 5 to 20 mm on both of the right and left sides.

Further, the liquid impervious sheet 11 may has on an inside thereof, in particular on a surface of the absorbent body 56 side thereof, an excretion indicator 80 that changes in color when absorbing a liquid.

(Barrier Cuffs)

Barrier cuffs 60 are band-like members that extend in the entire longitudinal direction along the both sides of the inner body 200. The barrier cuffs 60 are provided to block urine or loose stool moving laterally over the face sheet 30 and to prevent lateral leakage. In this embodiment, the barrier cuffs 60 stand from the side portions of the inner body 200, root sections thereof stand diagonally toward the central portion of the inner body 200 in the lateral direction, and central to tip portions thereof stand diagonally outward in the lateral direction.

More specifically, the barrier cuffs 60 are each configured such that a band-like barrier sheet 62 identical in length to the inner body 200 in the longitudinal direction, is turned down and doubled in the lateral direction, and that a plurality of elongated resilient and elastic members 63 are fixed on the turndown part and surrounding part of the doubled sheet, in an extended state in the longitudinal direction at intervals therebetween in the lateral direction. In each of the barrier cuffs 60, an end on an opposite side of the turndown part in the lateral direction is set as an attachment part 65 that is fixed on the side edges of the inner body 200 on underside surfaces, and the part other than the attachment part 65 is set as a projecting part 66 that projects from the attachment part 65 (on the turndown part side). The projecting part 66, on each end in the longitudinal direction, includes: a base portion that extends from the attachment part 65 through the side of the inner body 200 to the front surface of the side part of the face sheet 30 and is fixed to the front surface of the side part of the face sheet 30 at a front-back fixed portion 67 with the use of a hot-melt adhesive or heat sealing; and a tip portion that is turned down from a tip of the base portion toward outward in the longitudinal direction and is fixed to the base portion. The projecting part has an intermediate portion as a non-fixed free portion (internal side free portion) in the longitudinal direction, and the elongated resilient and elastic members 63 are fixed in an extended state to the free portion in the longitudinal direction.

The barrier sheet 62 may use favorably a soft nonwoven fabric with excellent uniformity and concealment properties such as spun bond nonwoven fabrics (SS, SSS, and the like), SMS nonwoven fabrics (SMS, SSMMS, and the like), or melt-blown nonwoven fabrics, which are made water-repellent as required using silicon or the like. A basis weight of fibers in the fabric is preferably about 10 to 30 g/m². The elongated resilient and elastic members 63 may use rubber threads or the like. If spandex rubber threads are used, a thickness thereof is preferably 470 to 1,240 dtex, more preferably 620 to 940 dtex. The spandex rubber threads are preferably fixed at an extension ratio of preferably 150 to 350%, more preferably 200 to 300%. In addition, as shown in the figures, a water-proof film may be interposed in the two-fold barrier sheet.

The number of the elongated resilient and elastic members 63 is preferably 2 to 6, more preferably 3 to 5, at each of free portions of the barrier cuffs 60. The arrangement interval 60d is appropriately set between 3 to 10 mm. In such an arrangement, the barrier cuffs 60 are likely to contact the skin of the wearer in areas with the elongated resilient and elastic members 63. The barrier cuffs 60 may also have the elongated resilient and elastic members 63 at the base portions as well as the tip portions.

The attachment parts 65 of the barrier cuffs 60 may be fixed to appropriate members of the inner body 200, such as the face sheet 30, the liquid impervious sheet 11, the absorbent element 50, or the like.

In the thus configured barrier cuffs 60, contraction forces of the elongated resilient and elastic members 63 act to bring the both front-back ends of the barrier cuffs closer to each other. However, the both longitudinal ends of the projecting parts 66 are fixed so as not to stand, whereas portions between the both ends are not fixed as free portions. Accordingly, the barrier cuffs 60 stand such that only the free portions contact the skin of a wearer as shown in FIG. 3. In particular, with the attachment parts 65 located on the underside of the inner body 200, the barrier cuffs 60 stand so as to open outward in the lateral direction at the crotch portion and a surrounding portion thereof, and therefore the barrier cuffs 60 contact by area the peripheries of legs of a wearer, thereby resulting in an increased fit.

Figure 7:
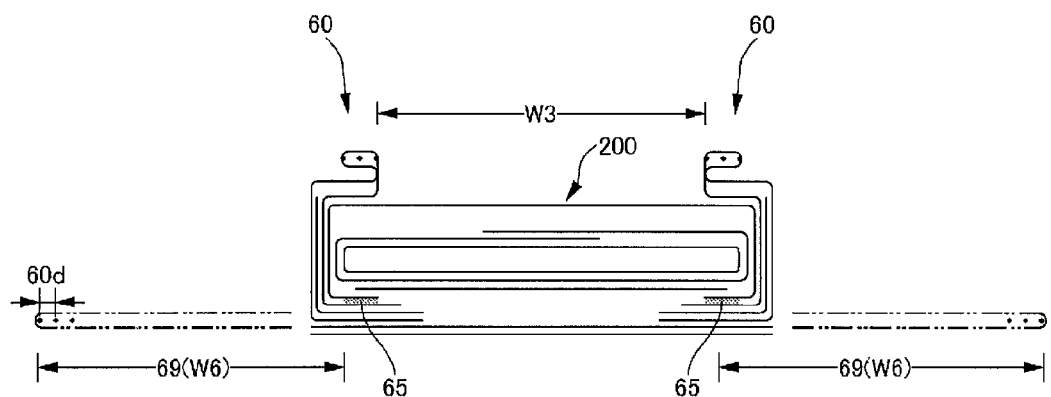
FIG. 7 is a cross-section view of the major components of the underpants type disposable diaper.

The dimensions of the barrier cuffs 60 can be decided as appropriate. In disposable diapers for babies and infants, as shown in FIG. 7 for example, an erection height W6 of the outer barrier cuff 60 (a length of the projecting part 66 in the lateral direction of the open diaper) is preferably 15 to 60 mm, in particular preferably 20 to 40 mm. In addition, when the barrier cuffs 60 are flatly folded in parallel to the top surface of the top sheet 30, a separation distance W3 between folding lines located at innermost positions in the barrier cuffs 60 is preferably 60 to 190 mm, in particular preferably 70 to 140 mm.

Alternatively, the barrier cuffs may be provided doubly (in two lines) on each of the right and left sides of the inner body 200, unlike the illustrated embodiment.

(Absorbent Element)

The absorbent element 50 has the absorbent body 56 and a package sheet 58 that envelops the entire absorbent body 56. The package sheet 58 may not be arranged.

(Absorbent Body)

The absorbent body 56 can be formed by a fiber assembly. Such a fiber assembly may use accumulated short fibers such as fluff pulp, synthetic fibers or the like, or may use a filament assembly obtained by opening as necessary a tow (fiber bundle) of synthetic fibers such as cellulose acetate or the like. A basis weight of fibers may be about 100 to 300 g/m² for accumulated fluff pulp or short fibers, for example, and may be about 30 to 120 g/m² for a filament assembly, for example. A fineness of synthetic fibers is 1 to 16 dtex, preferably 1 to 10 dtex, more preferably 1 to 5 dtex, for example. If a filament assembly is used, filaments may be non-crimped fibers but preferably are crimped fibers. A degree of crimping of the crimped fibers may be about 5 to 75 crimps per inch, preferably about 10 to 50 crimps per inch, and more preferably about 15 to 50 crimps per inch, for example. In many cases, uniformly crimped fibers are used. Preferably, the absorbent body 56 has high-absorbent polymer particles dispersed and retained therein.

Figure 1:
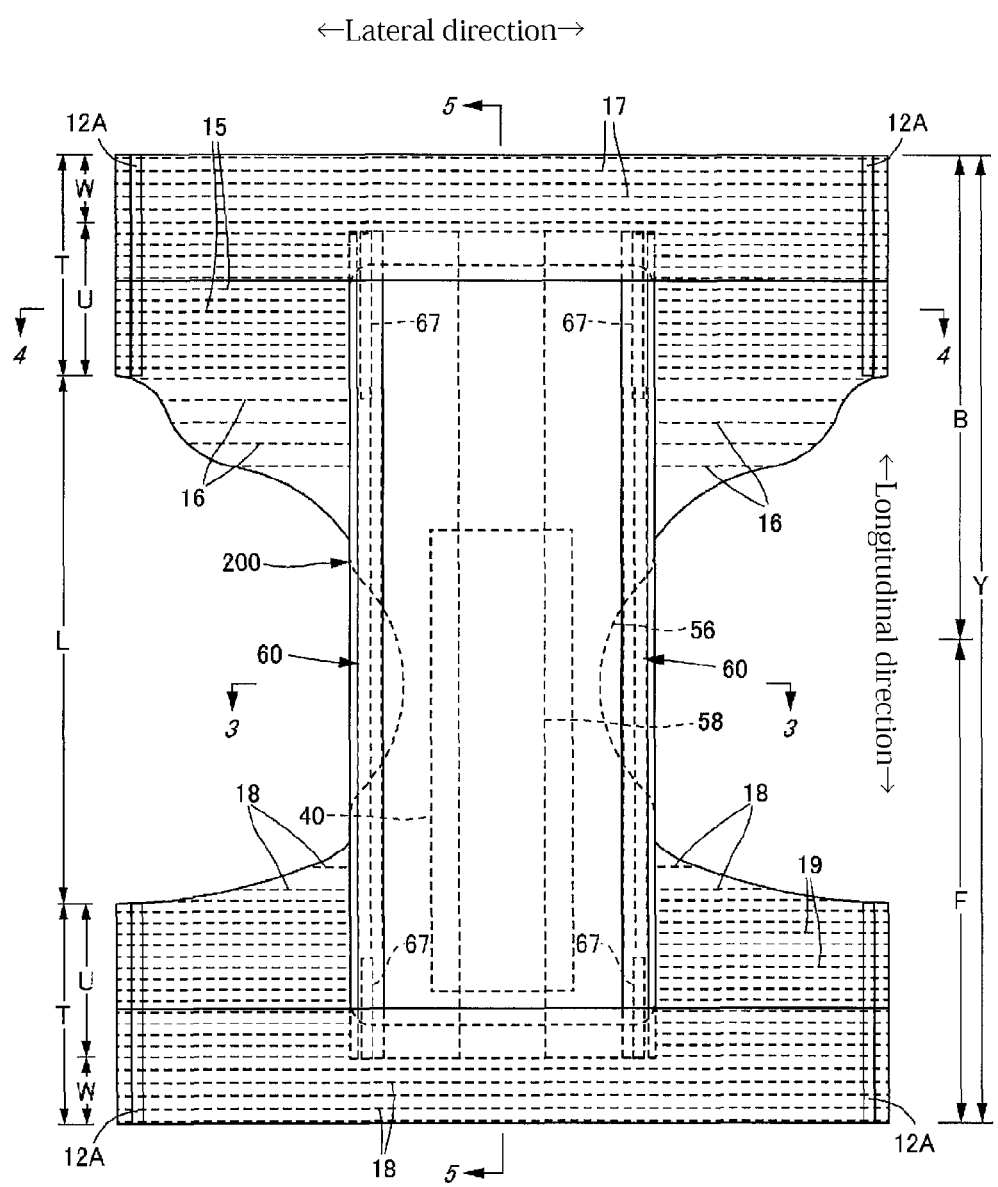
FIG. 1 is a plane view of an opened underpants type disposable diaper, showing an internal surface of the diaper.
Figure 2:
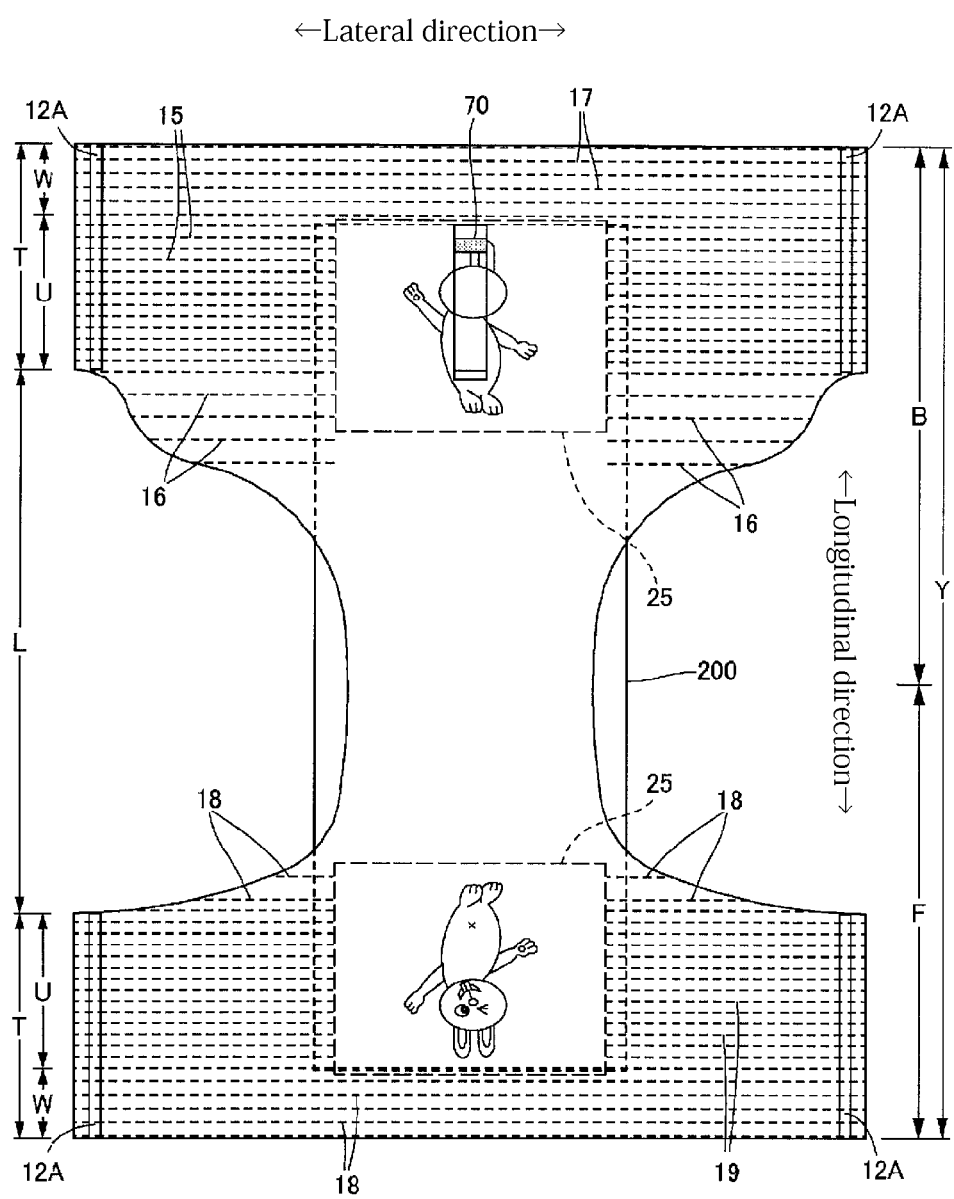
FIG. 2 is a plane view of the opened underpants type disposable diaper, showing an external surface of the diaper.

The absorbent body 56 may be rectangular. However, as shown in FIG. 1, the absorbent body 56 is preferably formed in the shape of a sandglass including a front end portion, a back end portion, and a narrower portion between the front and back end portions, the narrower portion being narrower than the front and back end portions. This improves the absorbent body 56 and the barrier cuffs 60 in fit property around the legs of a wearer.

The size of the absorbent body may be decided as appropriate, and preferably, the absorbent body extends to the peripheral edge of the inner body or a neighboring portion of the same in the longitudinal and lateral directions.

(High-Absorbent Polymer Particles)

The absorbent 56 can partly or entirely contain high-absorbent polymer particle. The high-absorbent polymer particle may be not only "particle" but also "powder". The high-absorbent polymer particle may be identical in particle diameter as particles used in this kind of disposable diaper, and is 1,000 µm or less, in particular desirably 150 to 400 µm. There are no particular limits on a material for the high-absorbent polymer particle, and a preferred material has 40 g/g or more in water absorption capacity. The high-absorbent polymer particle may be based on starch, cellulose or synthetic polymer, and may use starch-acrylic acid (salt) graft copolymer, saponified product of starch-acrylonitrile copolymer, crosslinked sodium carboxymethyl cellulose, acrylic acid (salt) polymer, or the like. A shape of the high-absorbent polymer particles is preferably a commonly used particulate shape and powder shape, and may also be any other shape.

The high-absorbent polymer particle preferably delivers a water absorption speed of 40 seconds or less. If the water absorption speed exceeds 40 seconds, a backflow phenomenon becomes prone to occur, where a liquid having been supplied to the absorbent body 56 flows back out of the absorbent body 56.

In addition, the high-absorbent polymer particle preferably has a gel strength of 1,000 Pa or more. This prevents effectively a sticky feel after absorption of a liquid even if the absorbent body 56 is high in bulk.

A basis weight of the high-absorbent polymer particle may be decided as appropriate in accordance with an absorption capacity required for the absorbent body 56, and may be 50 to 350 g/m², although it is not always defined so. If the basis weight of the polymer is less than 50 g/m², it is difficult to ensure a sufficient absorption capacity. With a basis weight of more than 350 g/m², the high-absorbent polymer particle becomes saturated in effectiveness.

If necessary, the high-absorbent polymer particle can be adjusted in density or amount of dispersion in the planar direction of the absorbent body 56. For example, an amount of dispersion may be made larger at a liquid excreted portion than other portions. With regard to a difference between the sexes, the dispersion density (amount) may be increased at the front side portion for men or increased at the middle portion for women. The polymer may not exist locally (for example, in spots) in the absorbent body 56 along the planar direction.

(Package Sheet)

The package sheet 58 may use any of materials such as tissue paper, in particular preferably crepe paper, a nonwoven fabric, a polyethylene laminated nonwoven fabric, a foraminous sheet, and the like. The package sheet 58 desirably is a finely woven sheet so as not to let the high-absorbent polymer particle pass through. If the package sheet 58 uses any nonwoven fabric instead of crepe paper, the nonwoven fabric is in particular preferably a hydrophilic SMS nonwoven fabric (SMS, SSMMS, or the like) that made from polypropylene, a polyethylene/polypropylene composite material, or the like. The material for the package sheet 58 desirably has a basis weight of 5 to 40 g/m², in particular 10 to 30 g/m².

The packaging mode of the package sheet 58 may be determined as appropriate. From the viewpoints of ease of manufacture and prevention of leakage of the high-absorbent polymer particle from front and back end edges and the like, it is preferred to surround and wrap cylindrically the absorbent body 56 with the package sheet 58 at front and back sides and both lateral sides; extend front and back edge portions of the package sheet 58 off from the front and back sides of the absorbent 56; and press the extended portions of the package sheet 58 in a longitudinal direction and join together the package sheet 58 and the absorbent body 56 with a hot-melt adhesive or the like.

(Outer Sheet)

Figure 8:
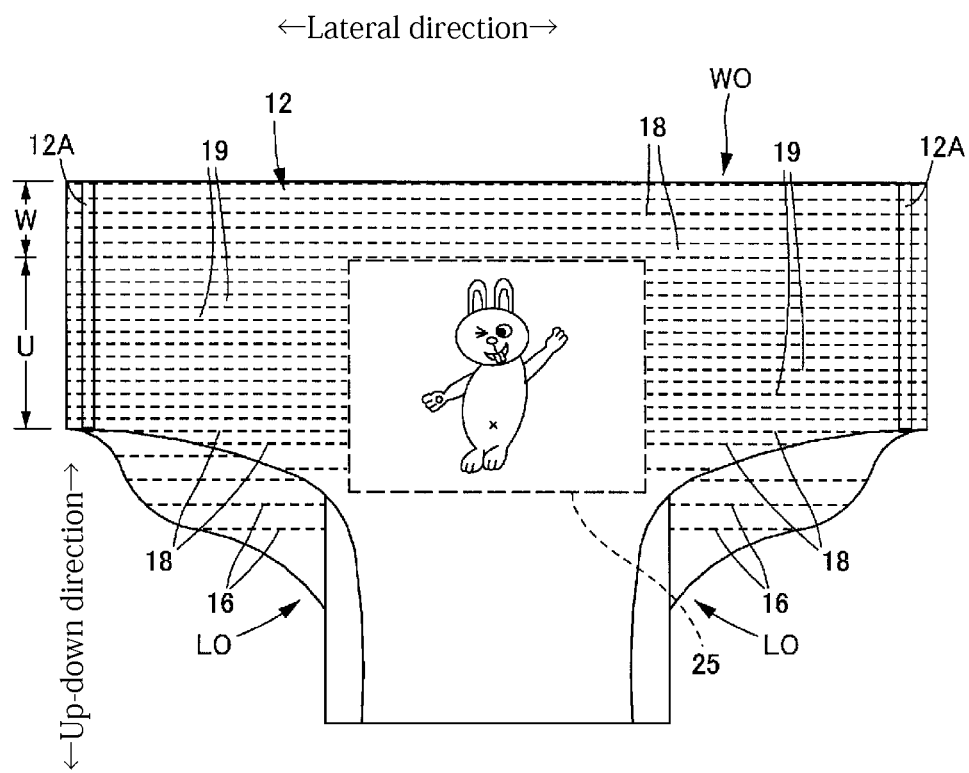
FIG. 8 is a front view of the diaper in a product state.
Figure 9:
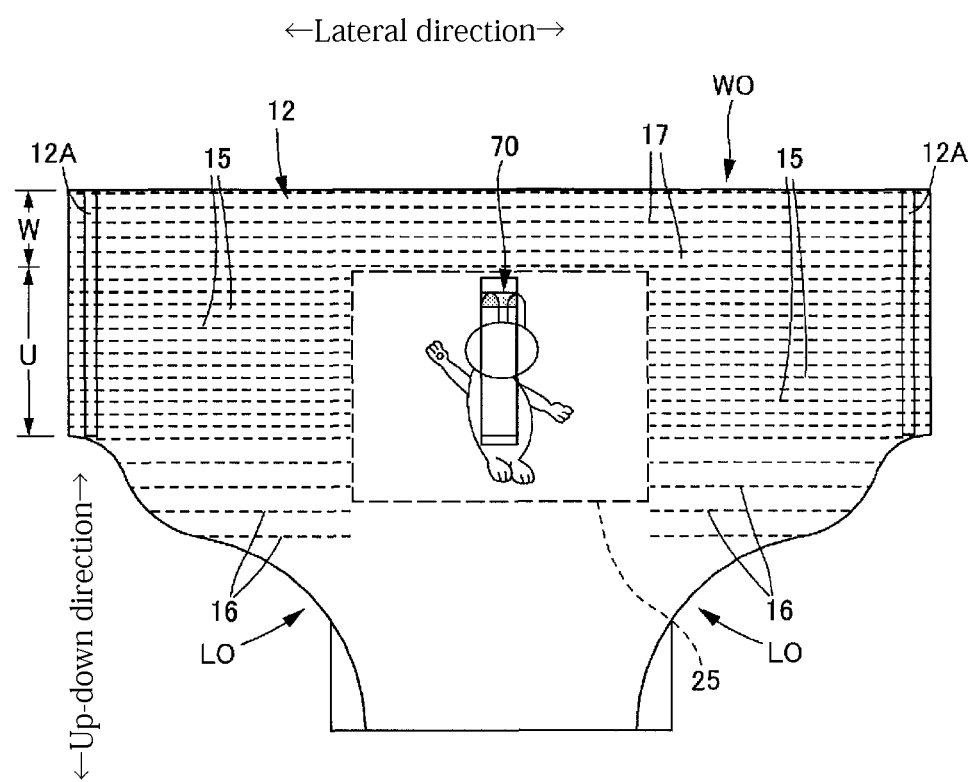
FIG. 9 is a rear view of the diaper in a product state.

An outer sheet 12 has a front body part F extending from a crotch portion toward the ventral side and a back body part B extending from the crotch portion toward the back side. These front body part F and back body part B are joined together at both sides, thereby to form a waist opening WO for letting the trunk of a wearer pass through and a pair of right and left leg openings LO for letting the legs of a wearer pass through, as shown in FIGS. 8 and 9. Reference numeral 12A denotes joint portions (hereinafter, these portions will be referred to as side seal portions also). The crotch portion here refers to a middle portion in the longitudinal direction ranging from a waist end edge of the front body part to a waist end edge of the back body part in the opened diaper. Front and back side portions of the crotch portion constitute the front body part F and the back body part B, respectively.

The outer sheet 12 has a trunk surrounding portion T that is determined as a longitudinal area ranging from the waist opening WO to upper ends of the leg openings LO, and an intermediate portion L that is determined as a longitudinal area forming the leg openings LO. The trunk surrounding portion T can be conceptually divided into a "waist side end portion" W and a "trunk lower portion" U. Lengths of the portions vary depending on the size of a product and can be determined as appropriate. As one example, the waist side end portion W may have a length of 15 to 40 mm, and the trunk lower portion U may have a length of 65 to 120 mm. In addition, the intermediate portion L is narrowed at both side edges thereof along the legs of a wearer, into which the legs of a wearer are entered. As a result, the outer sheet 12 is shaped in the shape of an almost sand glass as a whole. The degree of narrowing of the outer sheet 12 can be determined as appropriate. The outer sheet 12 is preferably made narrower than a width of the inner body 200 at a narrowest section thereof for simple appearance, as shown in the mode shown in FIGS. 1 to 10. Alternatively, the outer sheet 12 may be wider than the width of the inner body 200 even at the narrowest section.

The outer sheet 12 is formed by sticking together two sheet base materials 12S and 12H with an adhesive such as a hot-melt adhesive, as shown in FIGS. 3 to 5. The inner sheet base material 12H positioned inside extends only to the edge of the waist opening WO, whereas the outer sheet base material 12S goes beyond the waist side edge of the inner sheet base material 12H and is turned down to the inside of the same. The turndown portion 12r extends to cover up to the waist side end portion of the inner body 200.

The sheet base materials 12S and 12H have no particular limitation in other respects, but preferably use a nonwoven fabric. Such a nonwoven fabric has no particular limitation in raw fibers therefor. For example, the raw fibers may be any of synthetic fibers based on olefin such as polyethylene or polypropylene, polyester, polyamide or the like, recycled fibers such as rayon or cupra, natural fibers such as cotton or the like, mixed or composite fibers of two or more of the foregoing fibers. Further, the nonwoven fabric may be produced by any processing method. For example, the processing method may be any of known methods such as a spun lace method, spun bonding method, thermal bonding method, melt-blown method, needle punching method, air-through method, point bonding method, and the like. If any nonwoven fabric is used, the nonwoven fabric preferably has a fiber basis weight of about 10 to 30 g/m².

In addition, if any design print is provided to the odor eliminating printed sheet 25 described later, the outer sheet 12 preferably has a total basis weight of about 20 to 60 g/m² and has a total light transmission rate defined by JIS K 7105 of 40% or more, in particular 50% or more, so that the design can be seen from the external surface of the product through the outer sheet 12.

In addition, for an enhanced fit at the waist of a wearer, the outer sheet 12 has elongated resilient and elastic members 15 to 19 such as rubber threads at a predetermined extension ratio between the two sheet base materials 12S and 12H. The elongated resilient and elastic members 15 to 19 may use synthetic rubber or natural rubber. Using a hot-melt adhesive or heat sealing or ultrasonic attachment in various application methods, it is possible to attach the two sheet base materials 12S and 12H of the outer sheet 12 to each other, and sandwich and fix the elongated resilient and elastic members 15 to 19 between the sheet base materials 12S and 12H. It is not preferred to fix firmly the entire outer sheet 12, which deteriorates the sheet in texture. It is preferred to combine the foregoing attachment modes such that the elongated resilient and elastic members 15 to 19 are firmly attached and other parts are not attached or are weakly attached.

More specifically, in the waist end portions (upper end portions) W of the back body part B and the front body part F, a plurality of waist resilient and elastic members 17 and 18 are continuously fixed in the entire lateral direction between an internal surface of the inner sheet base material 12H and an outer surface of a turndown section 12r of the outer sheet base material 12S, at intervals therebetween in the up-down direction and in a state of being extended in the lateral direction at a predetermined extension ratio. In addition, out of the waist resilient and elastic members 17 and 18, one or more members disposed in a section adjacent to the trunk lower portion U may overlap the inner body 200, or may be disposed on both sides of the trunk lower portion U in the lateral direction except for an central portion in the lateral direction overlapping the inner body 200. As the waist resilient and elastic members 17 and 18, about 3 to 22 rubber threads with a fineness of about 155 to 1,880 dtex, in particular about 470 to 1,240 dtex (in the case of synthetic rubber. For natural rubber, about 0.05 to 1.5 $mm^2$, particularly about 0.1 to 1.0 $mm^2$, in cross-section area), are preferably fixed at intervals of 4 to 12 mm at an extension ratio of about 150 to 400%, in particular about 220 to 320%. In addition, the waist resilient and elastic members 17 and 18 do not need to be all the same in fineness and extension ratio, and may be different in fineness and extension ratio between the upper and lower portions of the waist end portion W, for example.

In addition, in the trunk lower portions U of the front body part F and the back body part B, a plurality of elongated resilient and elastic members 15 and 19 are continuously fixed in the entire lateral direction between an external side surface of the inner sheet base material 12H and an internal side surface of the outer sheet base material 12S, at the upper portion and the both side portions in the lateral direction except for a central portion in the lateral direction overlapping the inner body 200, at intervals therebetween in the up-down direction and in a state of being extended in the lateral direction at a predetermined extension ratio.

As the elongated resilient and elastic members 15 and 19 of the trunk lower portion U, about 5 to 30 rubber threads with a fineness of about 155 to 1,880 dtex, in particular about 470 to 1,240 dtex (in the case of synthetic rubber. For natural rubber, about 0.05 to 1.5 $mm^2$, particularly about 0.1 to 1.0 $mm^2$, in cross-section area), are preferably fixed at intervals of 1 to 15 mm, in particular 3 to 8 mm, at an extension ratio of about 200 to 350%, in particular about 240 to 300%.

In addition, in the intermediate portion L of the front body part F and the back body part B, a plurality of elongated resilient and elastic members 16 are continuously fixed in the entire lateral direction between the external side surface of the inner sheet base material 12H and the internal side surface of the outer sheet base material 12S, at the both side portions in the lateral direction except for a central portion in the lateral direction overlapping the inner body 200, at intervals therebetween in the up-down direction and in a state of being extended in the lateral direction at a predetermined extension ratio.

As the elongated resilient and elastic members 16 and 18 of the intermediate portion L, about 2 to 10 rubber threads with a fineness of about 155 to 1,880 dtex, in particular about 470 to 1,240 dtex (in the case of synthetic rubber. For natural rubber, about 0.05 to 1.5 $mm^2$, particularly about 0.1 to 1.0 $mm^2$, in cross-section area), are preferably fixed at intervals of 5 to 40 mm, in particular, 5 to 20 mm, at an extension ratio of about 150 to 300%, in particular about 180 to 260%.

As illustrated, when the elongated resilient and elastic members 15, 19, 16, and 18 are provided at the trunk lower portion U and the intermediate portion L on the both sides in the lateral direction except for the central portion in the lateral direction overlapping the inner body 200, it is preferably prevented that the inner body 200 is contracted beyond necessity in the lateral direction and therefore is deteriorated in appearance due to swelling or is decreased in absorption capability. In this mode, the resilient and elastic members may be arranged only at the both sides of the article in the lateral direction, or the resilient and elastic members may be arranged across the inner body 200 from one side to the other side in the lateral direction and be cut out at the central portion in the lateral direction overlapping the inner body 200 so as not to exercise a stretching force (which is virtually equal to not providing the resilient and elastic members). As a matter of course, the arrangement mode of the elongated resilient and elastic members 15, 16, 18, and 19 is not limited to the foregoing example. Alternatively, some or all of the elongated resilient and elastic members 15, 16, 18, and 19 may be arranged at the trunk lower portion U across the inner body 200 from one side to the other side in the lateral direction so as to exert a stretching force on the entire trunk lower portion U in the lateral direction.

In addition, if the elongated resilient and elastic members 15 to 19 straddle the odor eliminating printed sheet 25 with a design print described later, when the elongated resilient and elastic members 15 to 19 use rubber containing titanium oxide, the rubber preferably has a low content (2% or less, for example) of titanium oxide. Otherwise, the rubber preferably does not contain titanium oxide at all.

(After-Treatment Tape)

An after-treatment tape 70 (fixing means) is arranged on an external surface of the back body part B of the outer sheet 12 at a central portion in a lateral direction. The after-treatment tape 70 is intended to fix the rolled or folded diaper in which the face sheet 30 and the front body part F are positioned inside. In the general after-treatment tape 70, as shown in FIG. 5, the base portion 71 is fixed with an adhesive or the like to the external surface of the outer sheet 12, and a portion nearer to the tip portion than the base portion 71 is folded in three (Z-shaped in cross section) or two, and the folded and overlaid portion is fixed with a temporary bonding adhesive 72 so as to be capable of being separated (temporary fixation). In addition, the after-treatment tape 70 has a tab part 73 in an opaque color such as white at the tip portion thereof, and has a transparent or translucent part other than the tab part 73. This allows a printed design described later to be seen from the external surface side of the after-treatment tape 70 through the transparent or translucent part of the after-treatment tape 70. Although the after-treatment tape 70 may be structured as appropriate, the after-treatment tape 70 in the illustrated embodiment is structured such that the entire part is formed by joining a plurality of transparent or translucent base materials in a longitudinal direction and then a colored tape 74 is stuck to the tab part 73.

At disposal, the diaper is rolled or folded such that the face sheet 30 and the front body part F are positioned inside, and the folded and overlaid portions of the after-treatment tape 70 are separated and extended. Then, the after-treatment tape 70 is wound around the rolled or folded diaper from the back body part B through the waist opening WO to the external surface of the opposite side, and is fixed with an adhesive. The after-treatment tape 70 has in particular preferably a threefold shape so as to be folded compact when not used and to be extended longwise for use.

Although not shown, a tape type disposable diaper is worn and fixed to the body of a wearer by attaching fastening tapes projecting from the both sides of the back body part to the external surface of the ventral side part. After use, the tape type disposable diaper is detached from the body of the wearer by removing the fastening tapes from the external surface of the ventral side part. Then, the diaper is rolled or folded from the crotch portion side such that the front body part and the back body part overlay on each other and that the front body part is positioned inside, and then the fastening tapes on the both sides of the back body part are wound around the rolled or folded diaper from the both sides and are fixed to the external surface of the diaper. Accordingly, the fastening tapes on the tape type disposable diaper also serve as after-treatment tapes.

Figure 12:
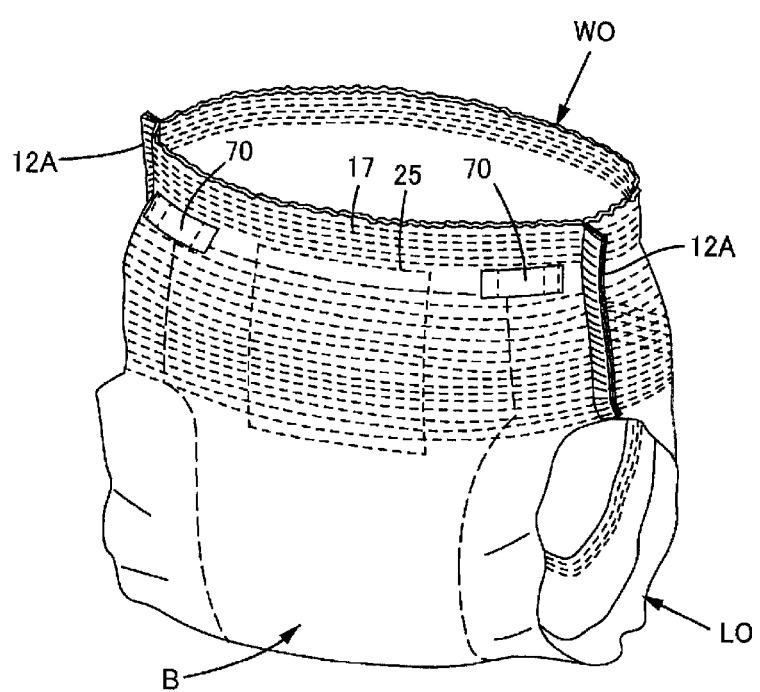
FIG. 12 is a perspective view of a back side of an underpants type disposable diaper in another mode.

In addition, as shown in FIG. 12, the underpants type disposable diaper may have the after-treatment tape 70 on each side of the back body part B, as in the tape type disposable diaper with the fastening tapes. In this case, the diaper is rolled or folded such that the face sheet 30 and the front body part F are positioned inside, and the after-treatment tapes 70 are each pull out and wound around the rolled or folded diaper from the both sides and then are fixed on the external surface of the opposite side.

The fixing means for the after-treatment tape 70 or the like may be arranged on the front body part F or both on the back body part B and the front body part F.

(Odor Eliminating Printed Sheet)

An odor eliminating printed sheets 25 with a printed design or the like is interposed between the liquid impervious sheet 11 and the outer sheet 12 (including the interlayer space of the outer sheet 12). When the odor eliminating printed sheet 25 is positioned on the back surface side of the liquid impervious sheet 11, fine pores of the deodorant particle are not filled with a liquid content of excretion even after use (after absorption), thereby to exert an odor eliminating effect in accordance with a used amount of the deodorant particle. Even if a solvent of print ink or the like enters the fine pores of the deodorant particle, the fine pores are restored (activated) after drying of the ink, and the odor eliminating effect of the deodorant particle is hardly reduced by the influence of the ink. The outer sheet 12 may not be provided to thereby expose the odor eliminating printed sheet 25 to the outside. In addition, the odor eliminating printed sheet 25 in the illustrated example is smaller in area than the body part on which the same is arranged, and is separately arranged on the front body part F and the back body part B. Alternatively, the odor eliminating printed sheet 25 may be unified so as to be continuous from the front body part F through the crotch portion to the back body part B.

There are no particular limitations on size and shape of the odor eliminating printed sheet 25, but the odor eliminating printed sheet 25 preferably has a large area enough for exerting a sufficient odor eliminating effect. For example, the odor eliminating printed sheet 25 preferably has a width 25X of about 50 to 120% of a width of the absorbent body 56, and has a length 25Y of about 15 to 30% of an entire article length Y at least on either the ventral side or the back side. In addition, the odor eliminating printed sheet 25 preferably has a rectangular shape as in the illustrated example, from the viewpoint of causing no trim loss. However, the odor eliminating printed sheet 25 may be cut into any geometric shape such as a circle, an oval, a triangle, or a hexagon, or any other shape adapted to a circumference of the design.

There is no particular limitation on the odor eliminating printed sheet 25 as far as the same has an odor eliminating function, but the odor eliminating printed sheet 25 preferably has a sheet base material and a deodorant particle fixed to the sheet base material with an adhesive resin. Preferably in particular, the deodorant particle is partially uncovered with the adhesive resin on the external surface thereof. The odor eliminating printed sheet 25 performs an odor eliminating function at the part with the deodorant particle is bond. As a matter of course, alternatively, the odor eliminating printed sheet 25 may have a sheet base material which has been coated or impregnated with a deodorant solvent and then dried, or have a sheet base material that contains a deodorant component, that is, a film of deodorant resin or a fiber assembly of nonwoven fabric, paper or the like made from deodorant fibers.

The sheet base material for the odor eliminating printed sheet 25 may be a plastic film, nonwoven fabric, paper or the like, and preferably uses a bulky material with high air permeability. If a sheet base material for the odor eliminating printed sheet 25 is an air-permeable fiber assembly, in particular, paper made mainly from pulp fibers, the sheet base material itself has somewhat an odor eliminating effect by odor absorption, and increases a probability of contact of the deodorant particle with an odor as described later and improves an odor eliminating efficiency, owing to a large surface area and air permeability thereof. In the case of using a plastic film, the sheet base material desirably has moisture permeability for prevention of stuffiness. Nonwoven fabric and paper are preferred materials for moisture permeability thereof. If the odor eliminating printed sheet 25 is provided with a design print as described later, a nonwoven fabric material has a high smoothness for ease of printing, and it is preferable to use a paper material preferably that has a high strength and is less prone to cause ink bleeding. Preferred in particular are crepe paper (thin paper) with a basis weight of about 15 to 35 g/m$^2$ and a thickness of about 0.1 to 0.3 mm, and a nonwoven fabric with a basis weight of 10 to 25 g/m$^2$ and a thickness of about 0.1 to 0.3 mm (specifically, a spun bond nonwoven fabric with a fineness of about 1.0 to 3.0 dtex at a spun bond part and an SMS nonwoven fabric). The crepe paper as a sheet base material preferably has a crepe ratio of about 5 to 20%, in particular about 5 to 15%. With a crepe ratio of 20% or more, the crepe paper is high in ink fixation ratio but is prone to cause ink bleeding, and therefore is not suitable for a design print. With a crepe ratio of 5% or less, the crepe paper is less prone to let ink pass through, thereby leading to a smaller amount of fixed ink.

There is no particular limitation on the deodorant particle, but the deodorant particle preferably has a three-dimensional structure, a layered structure or a porous structure, for physical absorption (surface absorption) of an odor. The deodorant particle structure may allow only physical absorption or both physical absorption and chemical absorption. The deodorant particle may be any of publicly known deodorant particles, such as an activated carbon particle, a natural or synthetic zeolite particle (aluminosilicate particle with a three-dimensional framework structure), a layered structure particle made of zirconium phosphate, a three-dimensional particle made of silicate, and a zinc oxide particle. The porous particle preferably has a micropore diameter of 1 to 10 angstrom, in particular 3 to 10 angstrom, from the viewpoint of a surface area. With an excessively large micropore diameter, the particle is less effective due to decrease in surface area. With an excessively small micropore diameter, the particle is lowered in absorptive capacity for odor generating substances with large molecular sizes. Similarly, the porous deodorant particle preferably has a bulk density/real density of about 0.1 to 0.3. The porous deodorant particle with such a density preferably achieves excellent absorptive performance in particular for odor substances that become problematic at the time of disposal of disposable diapers, specifically, ammonia, hydrogen sulfide, methyl mercaptan, acetic acid, and the like. In the case of using such a deodorant particle as described above, the odor eliminating printed sheet 25 preferably has a deodorant particle content of 0.01 g/m$^2$ or more, in particular about 0.05 to 0.5 g/m$^2$, per unit area at a part with the deodorant particle thereof.

In addition, the deodorant particle preferably contains metallic ions that absorb chemically odor molecules. For example, the deodorant particle may be formed by substituting some or all of ion-exchangeable ions in the particle substance with silver ions, copper ions, zinc ions, or the like. More specifically, the deodorant particle may be formed by: substituting some or all of ion-exchangeable ions in zeolite with silver ions (Zeomic (registered trademark) produced by Shinanen Zeomic Co., Ltd. is commercially available); substituting some or all of ion-exchangeable ions in zirconium phosphate with copper ions ($Zr_3(PO_4.Cu^{2+})$); substituting some or all of ion-exchangeable ions in silicate with copper ions; zinc oxide particle; or substituting some or all of ion-exchangeable ions in silicate with zinc ions. One example of a formula for an odor eliminating reaction (chemical absorption) will be shown below. In this formula, odor molecules and metallic ions are subjected to coordinate bonding for formation of complex ions.

$$Cu^{2+} + H_2S \rightarrow H_2S: Cu^{2+}$$

When containing silver ions, the deodorant particle may turn into yellow by the action of humidity, sunlight, fluorescence, Nox, and the like. Therefore, in the case of using a deodorant formed by substituting some or all of ion-exchangeable ions in a particle substance with silver ions, it is preferred to employ at least one of the following arrangements (a) to (c):

(a) a content of silver ions per unit area of the odor eliminating printed sheet 25 is kept at 0.3 mg/m² or less to thereby suppress the degree of discoloration;

(b) yellow ink is used as a means for attachment of the deodorant particle to thereby make discoloration less noticeable; and (c) the sheet base material for the odor eliminating printed sheet 25 has a total light transmission rate of 50% or less, in particular 40% or less defined by JIS K7105, to thereby attach the deodorant particle only to a side surface of the liquid impervious sheet 11. This makes discoloration less noticeable on the external surface of the product. In the arrangement (c), the total light transmission rate may be kept low by adjusting a basis weight or formation of the sheet, and alternatively, the total light transmission rate may be lowered by printing the sheet with ink of white or another color on the entire surface (underprint).

There is no particular limitation on the adhesive resin as far as the same is capable of attaching the deodorant particle to the sheet base material, but the adhesive resin is preferably a urethane-based resin (polyurethane resin). Using such an adhesive resin with a high air permeability increases efficiency of contact of an odor with the deodorant particle, and therefore exerts a more excellent odor eliminating effect. The urethane-based resin can be obtained by letting an organic diisocyanate compound to react with a polymeric diol compound to synthesize urethane prepolymer and then reacting the same with a chain extender and a reaction inhibitor. Organic diisocyanate compounds usable for synthesis of a polyurethane resin include aliphatic diisocyanate compounds (for example, hexamethylene diisocyanate, 2,2,4-trimethyl hexamethylene diisocyanate, and the like), alicyclic diisocyanate compounds (for example, isophorone diisocyanate, hydrogenated xylylene diisocyanate, and the like), aromatic aliphatic diisocyanate compounds (xylylene diisocyanate, α,α,α',α'-tetramethylxylylene diisocyanate, and the like), and aromatic diisocyanate compounds (for example, toluylene diisocyanate, diphenylmethane diisocyanate, and the like).

The deodorant particle generally has an average particle diameter of 0.1 to 10 μm, preferably 2.0 to 8.0 μm, in particular preferably 2.0 to 5.0 μm (median size defined by JIS K 1474-2007), so that the deodorant particle is partially uncovered with adhesive resin on the external surface thereof to exert a sufficient odor eliminating effect, and that the deodorant particle can be easily produced. With an excessively small average particle diameter, the deodorant particle becomes difficult to handle. With an excessively large average particulate diameter, the deodorant particle is lowered in odor eliminating effect due to a smaller surface area. Therefore, after application and drying of ink, the sheet base material preferably has an ink film thickness of less than 2.0 μm so that most of the deodorant particle is exposed on the coating film of the adhesive resin. In particular preferably, the sheet base material has an ink layer thickness of about 1.0 to 1.5 μm with a sufficient odor eliminating effect. Further, the deodorant particle preferably accounts for 10 to 20 parts by weight with respect to 100 parts by weight of the adhesive resin.

The odor eliminating printed sheet 25 is arranged on the body part with the after-treatment tape 70. Specifically, the disposable diaper in the illustrated example has the after-treatment tape 70 arranged on the back body part B, and at the time of disposal, the diaper is rolled or folded and fixed such that the face sheet 30 and the front body part F are positioned inside as described above. In this disposal mode, an odor of excretion attached to the face sheet 30 and absorbed by the absorbent body 56 contacts the odor eliminating printed sheet 25 on the back body part B when the odor is emitted to the outside through the back body part B, whereby odor elimination can be performed more effectively. In addition, in the disposal mode of the rolled or folded diaper, the odor eliminating printed sheet 25 is positioned nearer to the outside to exert an odor eliminating effect also on an external odor. Therefore, to exert such an odor eliminating effect, if fixing means such as the after-treatment tape 70 is arranged on the front body part F unlike in the illustrated example, the odor eliminating printed sheet 25 needs to be also arranged on the front body part F. In addition, for such an odor eliminating effect, it is preferred that at least part of the odor eliminating printed sheet 25 overlaps the absorbent body 56. For example, the odor eliminating printed sheet 25 is preferably arranged at a central portion in the lateral direction of the absorbent body 56 as in the illustrated mode. Alternatively, the odor eliminating printed sheet 25 may not overlap the absorbent body 56.

Figure 10:
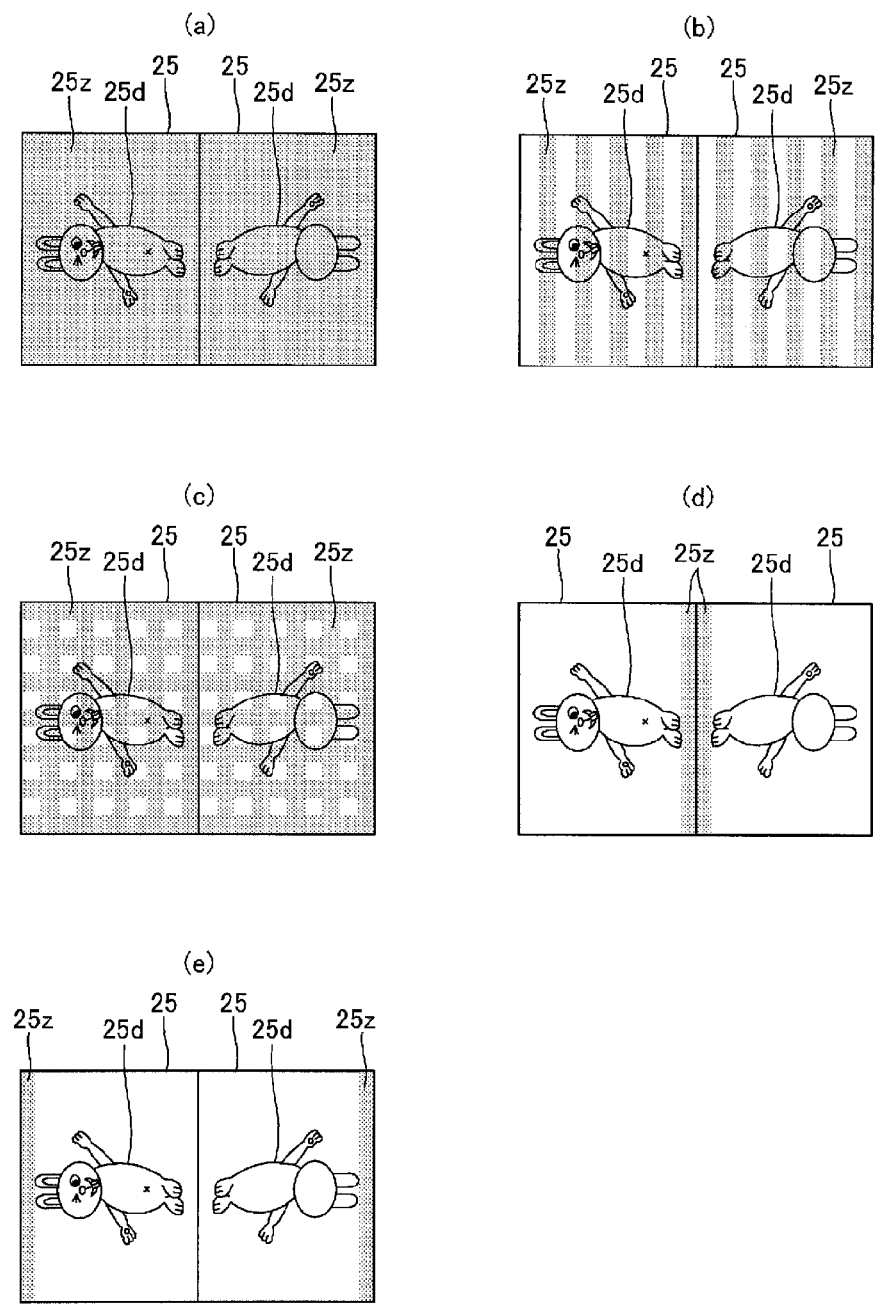
FIG. 10 is a plane view of an odor eliminating printed sheet, showing various print patterns.
Figure 11:
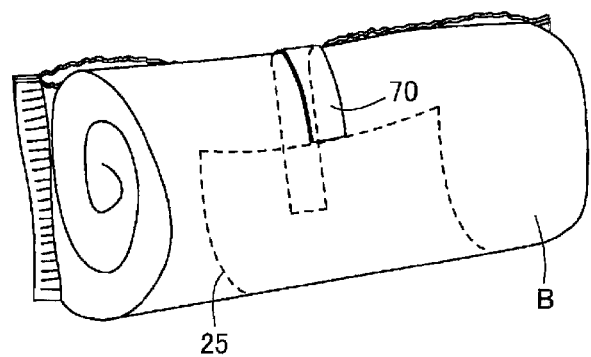
FIG. 11 is a schematic perspective view of the diaper in a disposal state.
Figure 13:
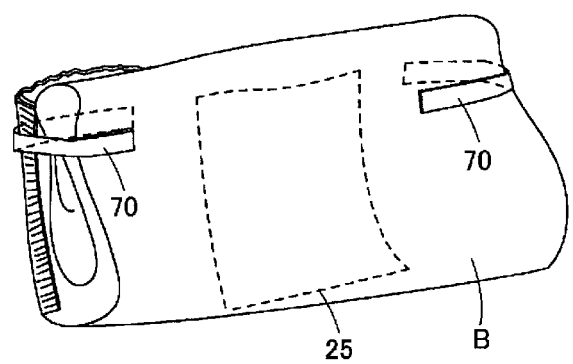
FIG. 13 is a schematic perspective view of the diaper in a disposal state.

More specifically, in the mode where the after-treatment tape 70 is arranged only at the central portion in the lateral direction as shown in FIGS. 1 to 11, the odor eliminating printed sheet 25 overlaps at least part of the base portion 71 of the after-treatment tape 70, preferably overlaps the entire base portion 71, and the overlapping part of the odor eliminating printed sheet 25 preferably overlaps the absorbent body 56. In addition, if the after-treatment tape 70 is arranged on the both sides as shown in FIG. 12, the odor eliminating printed sheet 25 is arranged such that a line linking the right and left after-treatment tapes 70 straddles the odor eliminating printed sheet 25. In either case, in the disposal modes of the rolled or folded diaper as shown in FIGS. 11 and 13, the odor eliminating printed sheet 25 is positioned so as to be higher in efficiency of contact with an odor, that is, is positioned on the outside of an odor generating source and closer to the external surface of the diaper.

The odor eliminating printed sheet 25 is attached to the liquid impervious sheet 11 on the front surface side thereof and the outer sheet 12 on the back surface side thereof. In the drawing, reference numeral 25B denotes sections to which an adhesive is applied. The mode of attachment to the sheets 11 and 12 can be decided as appropriate. Preferably, the odor eliminating printed sheet 25 is intermittently attached to the liquid impervious sheet 11 such that at least part of the odor eliminating printed sheet 25 is separated from the liquid impervious sheet 11 to form spaces between the two sheets, and that an area of attachment accounts for about 0 to 70%, in particular about 0 to 20%, of the area of the odor eliminating printed sheet 25. Specifically, the adhesive-applied sections 25B are arranged in a stripe pattern (a plurality of streaks are provided in parallel, horizontal stripes in the mode of FIG. 6) or in a grid pattern or the like, thereby forming adhesive-unapplied sections 25U. Accordingly, when such adhesive-unapplied sections are provided between the odor eliminating printed sheet 25 and the liquid impervious sheet 11 on the absorbent body 56 side, it is possible to form spaces for temporarily retaining an odor between the liquid impervious sheet 11 and the odor eliminating printed sheet 25, and to allow an odor from the liquid impervious sheet 11 side to efficiently contact the odor eliminating printed sheet 25, thereby enhancing an odor eliminating effect. It is preferred to form the adhesive-applied sections 25B in a virtually areal application pattern by using an application method such as curtain spraying, summit spraying, spiral spraying, with a large number of crossing fibers or threads of adhesive. This adhesive application pattern is excellent in terms of attachment strength due to a large attachment area, and allows smooth flows of air among the adhesive fibers or threads, thereby preventing the article from being significantly lowered in air permeability. In this adhesive application pattern, the adhesive generally has a basis weight of about 2 to 8 $g/m^2$, and a thickness of one fiber or one thread of about 0.02 to 1 mm.

Meanwhile, it is preferred to attach the odor eliminating printed sheet closely to the outer sheet 12 such that the attachment area accounts for about 80 to 100% of the area of the odor eliminating printed sheet 25. When the odor eliminating printed sheet 25 is closely attached to the outer sheet 12 on the external surface side, it is possible to exert an odor eliminating effect on an odor on the outside of the article. Therefore, the outer sheet 12 and the odor eliminating printed sheet 25 are preferably attached also by an adhesive application method such as curtain spraying, summit spraying, spiral spraying.

In addition, the odor eliminating printed sheet 25 has an area of 30% or more, more preferably 50% or more, of the area of the absorbent body 56 in the body part on which the same is arranged. It is further preferred that the odor eliminating printed sheet 25 has 80% or more of the area overlapping the absorbent body 56, from the viewpoint of efficiency of contact with an odor.

Even with a higher moisture permeability, specifically, 6,000 $g/m^2 \cdot 24$ h or more, the liquid impervious sheet 11 has excellent performance in odor eliminating to make an odor less annoying. Rather, the liquid impervious sheet 11 is preferably higher in moisture permeability to let an odor efficiently pass through the liquid impervious sheet 11 and contact the odor eliminating printed sheet 25.

Meanwhile, as a manufacturing method for the odor eliminating printed sheet 25 in the present invention, it is suggested that the sheet base material is printed with ink containing a deodorant particle, an adhesive resin, and a solvent as main components such that a thickness of an ink film formed on the sheet base material is smaller than the average particle diameter of the deodorant particle, thereby to obtain the odor eliminating printed sheet 25 containing the deodorant particle at the printed section. The thus obtained odor eliminating printed sheet can be supplied to a diaper manufacturing line and fixed to a predetermined section of the product in process with an adhesive or the like, thereby completing the foregoing diaper.

The ink may contain various inorganic pigments (for example, colored pigments such as oxidized titanium, colcothar, antimony red, cadmium yellow, cobalt blue, iron blue, ultramarine blue, carbon black, and black lead, and extender pigments such as calcium carbonate, kaolin, clay, barium sulfate, aluminum hydroxide, talc), and various organic pigments (for example, soluble azo pigment, insoluble azo pigment, azo lake pigment, condensed azo pigment, copper phthalocyanine pigment, condensed polycyclic pigment, and the like) used in general printing ink and paints.

Preferable solvents are organic solvents based on alcohol such as isopropyl alcohol or organic solvents based on ester such as ethyl acetate or n-butyl acetate, because those solvents have less impact on human body even if remaining on the odor eliminating printed sheet 25.

As a preferred composition of the ink, the deodorant agent constitutes 50 to 130 parts by weight and the solvent constitutes 600 to 1,500 parts by weight with respect to 100 parts by weight of the adhesive resin, so that the deodorant particle is partially uncovered with the adhesive resin on the external surface thereof to exert a sufficient odor eliminating effect, and that the deodorant particle can be easily produced. In addition, the odor eliminating printed sheet 25 preferably has a total content of the deodorant particle and the adhesive resin of about 0.10 to 0.60 $g/m^2$, in particular preferably, about 0.20 to 0.35 $g/m^2$, so that a part of the deodorant particle, which is uncovered with the adhesive resin, can be increased. If the diaper has a deodorant print also serving as a design print as described later, it is preferred to adjust a content of pigments in the ink as appropriate within a range of 0.5 to 50% by weight. With a larger ink film thickness, a part of the deodorant particle, which is uncovered with the adhesive resin, is decreased. Therefore, a content of pigments in the ink is desirably 10% by weight or less (2% by weight or more). In addition, the ink having been applied and dried (after volatilization of the solvent) has a content of the deodorant particle of preferably about 20 to 60% by weight. More preferably, the ink has almost equal contents of the deodorant particle and the components other than the deodorant particle (with a difference of ±10% by weight). In addition, the ink having been applied and dried (after volatilization of the solvent) has a content of the components other than the deodorant particle and the adhesive resin of preferably 30% by weight or less, more preferably 10% by weight or less. An application amount of the ink (before volatilization of the solvent) is preferably about 0.5 to 3.0 $g/m^2$ so that the film thickness of the ink having been applied and dried (after volatilization of the solvent) becomes less than 2.0 μm. In particular preferably, when an application amount of the ink (before volatilization of the solvent) is about 1.0 to 1.7 $g/m^2$, the film thickness of the ink having been applied and dried (after volatilization of the solvent) is about 1.0 to 1.5 μm.

At the time of manufacture of the odor eliminating printed sheet 25, it is possible to apply the adhesive resin to the sheet base material and then scatter the deodorant particle onto the adhesive resin. However, this method is not suitable for continuous manufacture because sticking efficiency and sticking power may be insufficient. Meanwhile, it is conventional practice to interpose a printed sheet including only a design print (containing no deodorant particle) between the liquid impervious sheet 11 and the outer sheet 12. Therefore, it is possible to realize the foregoing method for manufacturing the odor eliminating printed sheet of the present invention by simply mixing the deodorant particle into the ink for printing a design or any other dedicated ink different from the ink for printing a design, that is, it is possible to manufacture continuously the odor eliminating printed sheet 25 in an extremely easy manner with direct or advanced use of existing production facilities.

In addition, as will be understood from the foregoing description, it is possible to preferably eliminate the need for a design sheet by providing the odor eliminating printed sheet 25 with a design print. In this case, the odor eliminating printed sheet 25 may be provided with a deodorant print also serving as a design print on at least either of the front and back surfaces of the base material with the use of any ink containing the deodorant particle. Alternatively, the odor eliminating printed sheet 25 may be provided with a design print on at least either of the front and back surfaces of the base material and be provided with a deodorant print on at least either of the front and back surfaces of the base material with the use of any ink containing the deodorant particle (preferably transparent or translucent) different from the ink for printing the design. As a matter of course, the two methods can be combined. In the former method, there are some restrictions on section for containing the deodorant particle and quantity of the deodorant particle depending on the printing mode of the design (pattern or the like), whereas the latter method does not have such restrictions. In particular, it is preferred to provide the design print to the outer sheet 12 side surface of the odor eliminating printed sheet 25 thereby allow the design print to be more viewable from the outside of the article, and it is preferred to provide the print with the ink containing the deodorant particle to the liquid impervious sheet 11 side surface of the same so that an odor from the liquid impervious sheet 11 side can contact efficiently the deodorant particle. By providing the prints in such a manner, it is possible to prevent interference between the deodorant print with the ink containing the deodorant particle and the design print which deteriorates the diaper in odor eliminating effect and design expressivity. FIG. 10 shows examples of combinations of design print portions 25d and print portions with deodorant particle-contained ink 25z (hereinafter, referred simply to deodorant particle print portions also) in the case of using the latter method. In the example of FIG. 10(a), the design print portions 25d are provided on the back surface (external side surface) of the odor eliminating printed sheet 25, and the deodorant particle print portions 25z are provided on the entire front surface of the same (the liquid impervious sheet 11 side). In the example of FIG. 10(b), the design print portions 25d are provided on the back surface of the odor eliminating printed sheet 25 (external side surface), and the deodorant particle print portions 25z are provided in a horizontal stripe pattern on the front surface (the liquid impervious sheet 11 side). In the example of FIG. 10(c), the design print portions 25d are provided on the back surface (external side surface) of the odor eliminating printed sheet 25, and the deodorant particle print portions 25z are provided in a grid pattern on the front surface of the same (the liquid impervious sheet 11 side). In the examples of FIGS. 10(d) and 10(e), the design print portions 25d are provided on the back surface (external side surface) of the odor eliminating printed sheet 25, and the deodorant particle print portions 25z are provided on the same back surface at positions without the design print portions 25d (the peripheral edge of the odor eliminating printed sheet 25 in the illustrated example). In particular, if the deodorant particle print portions 25z are provided in a specific pattern so as to overlap the design print portions 25d as shown in the examples of FIGS. 10(b) and 10(c), the ink containing the deodorant particle is preferably transparent or translucent.

(Perforation for Exposure of the Odor Eliminating Printed Sheet)

Figure 14:
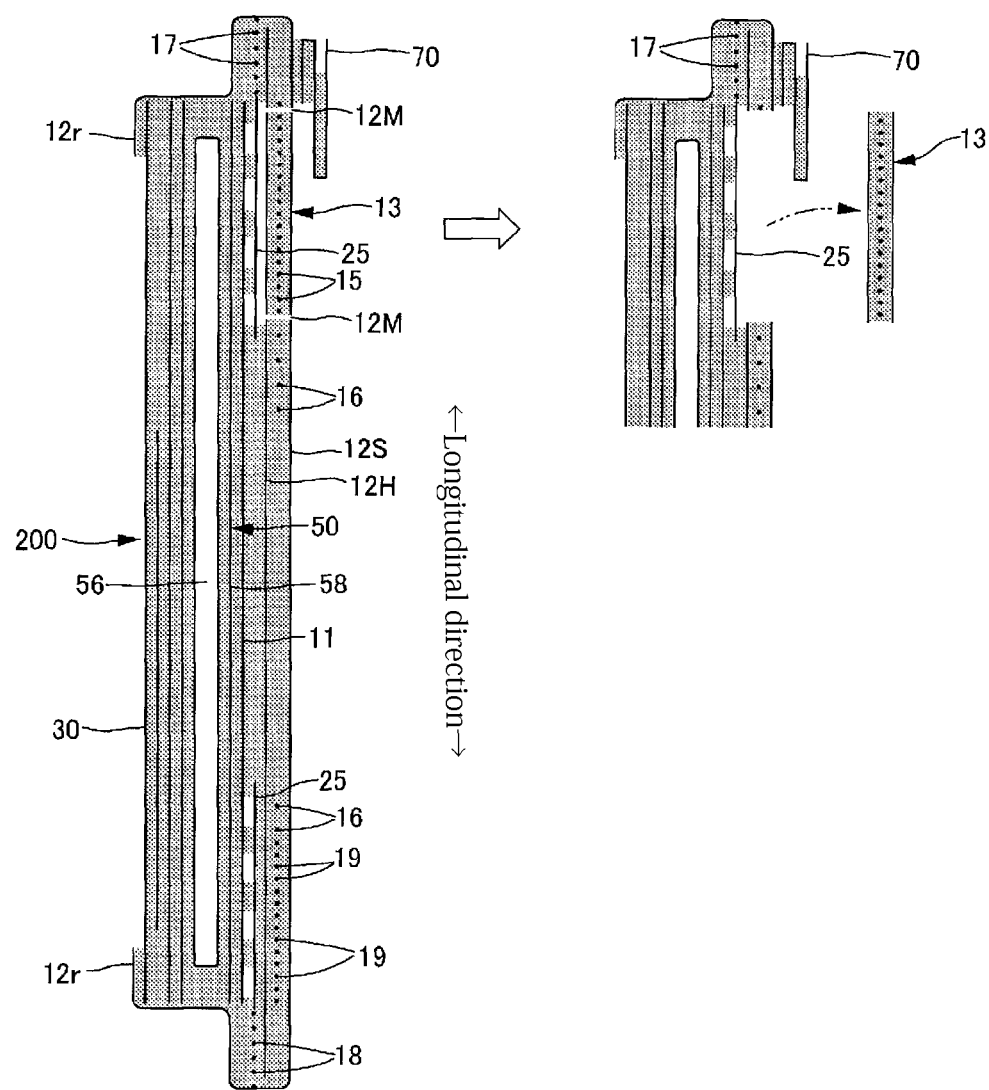
FIG. 14 is a cross-section view of FIG. 1 taken along 5-5, showing another underpants type disposable diaper.
Figure 15:
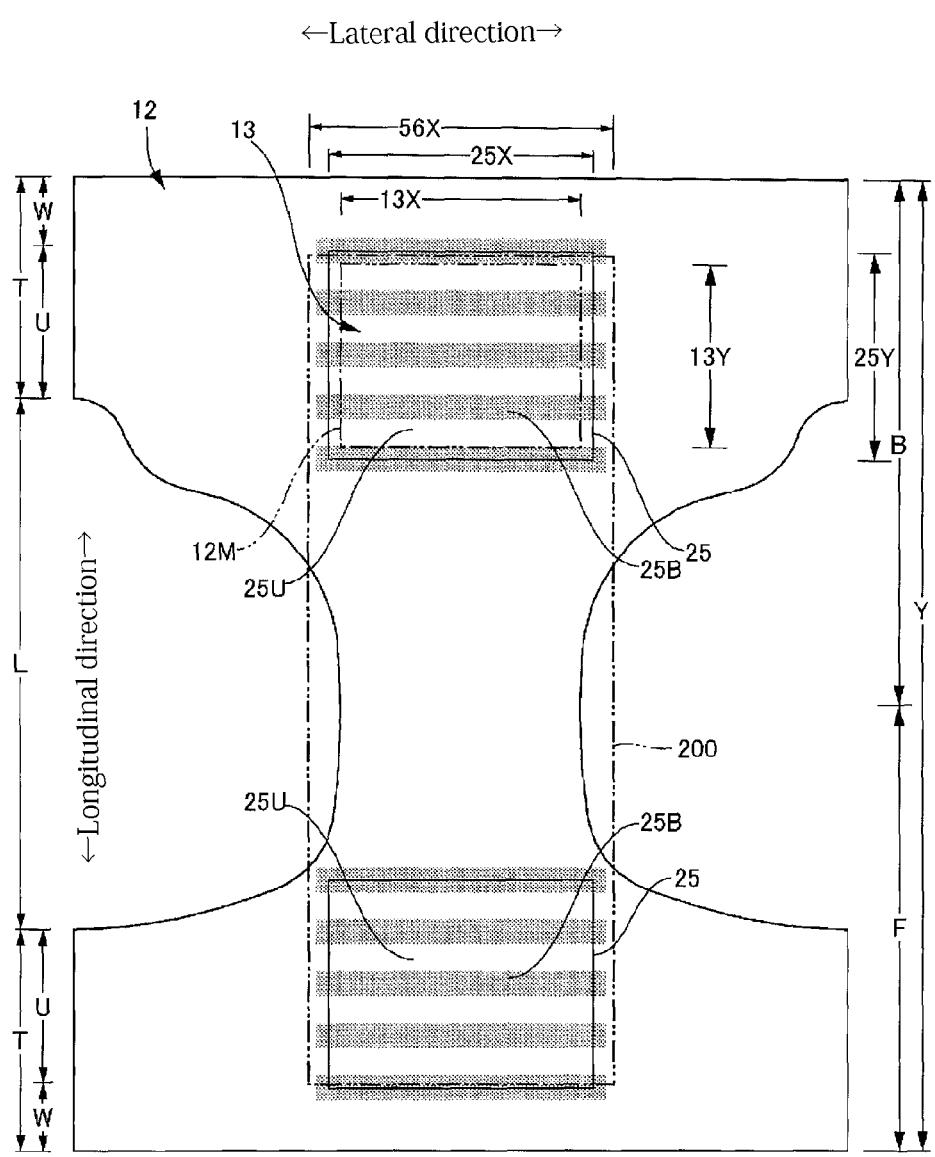
FIG. 15 is a plane view of the opened underpants type disposable diaper, showing major components of the diaper.
Figure 16:
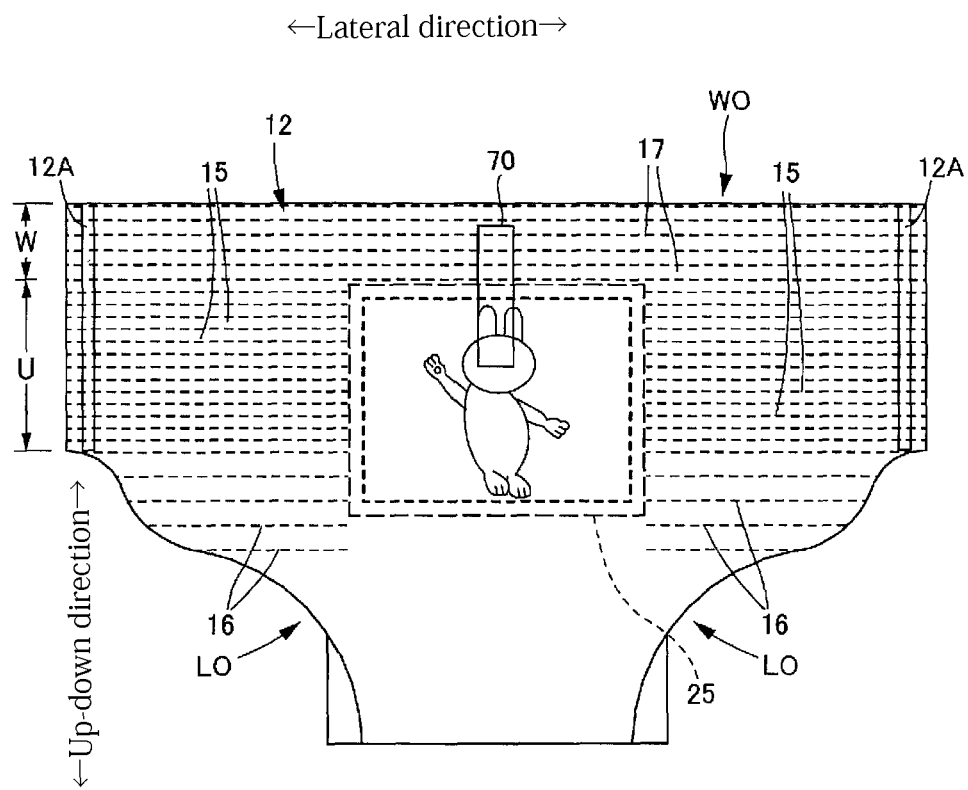
FIG. 16 is a rear view of the diaper in a product state.

In one preferred mode, as shown in FIGS. 14 to 16, the odor eliminating printed sheet 25 may be configured in such a manner that a perforation 12M is provided in a circumferential direction on the outer sheet 12 at an entire peripheral edge of a rectangular covering portion 13 overlapping the almost entire odor eliminating printed sheet 25, and that the covering portion 13 is cut along with the perforation 12M and turned up and removed to thereby expose the odor eliminating printed sheet 25 to the outside. In this mode, it is preferred that the part of the outer sheet 12 overlapping the covering portion 13 is attached detachably to the printed sheet (deodorant member) 25 or not attached to the same (illustrated example), and that the part of the outer sheet 12 not overlapping the covering portion 13 is firmly attached to the printed sheet 25 so as to be hard to detach. In this mode, particularly, when the deodorant print with ink containing the deodorant particle is provided to the outer sheet 12 side surface, it is possible to enhance an odor eliminating effect on an odor on the outside of the article.

The covering portion 13 may overlap only part of the odor eliminating printed sheet 25. In addition, the covering portion 13 may entirely overlap the odor eliminating printed sheet 25, or the covering portion 13 may partially or entirely extend off from the odor eliminating printed sheet 25.

There are no limitations on size and shape of the covering portion 13, but preferably, when the covering portion 13 is turned up, the odor eliminating printed sheet 25 as a deodorant member is widely exposed. In addition, the peripheral edge of the covering portion 13 is preferably positioned on the inside of the peripheral edge of the odor eliminating printed sheet 25 because it is undesired from the standpoint of appearance that the peripheral edge of the odor eliminating printed sheet 25 is exposed when the covering portion 13 is turned up. Specifically, as shown in FIG. 15, a width 13X of the covering portion 13 is preferably 50% or more of a width 25X of the odor eliminating printed sheet 25, and a length 13Y of the covering portion 13 is preferably 50% or more of a length 25Y of the odor eliminating printed sheet 25, and the covering portion 13 preferably contains 50% or more of the area of the odor eliminating printed sheet 25. In addition, the covering portion 13 is preferably almost identical in shape to the odor eliminating printed sheet 25. In the example of the illustrated mode, since the odor eliminating printed sheet 25 is rectangular, the covering portion 13 is preferably also rectangular. However, the shape of the covering portion 13 may not necessarily be adapted to that of the odor eliminating printed sheet 25. The covering portion 13 may have any geometric shape such as a circle, an oval, a triangle, or a hexagon, or any other shape along the peripheral edge of the design print.

If the after-treatment tape 70 is arranged in the mode in which the covering portion 13 is entirely removed from the outer sheet 12 as in the illustrated example, the base portion of the after-treatment tape 70 is preferably fixed to any part without the covering portion 13, for example, a part near the waist side of the covering portion 13.

In the thus configured disposable diaper, as shown in FIG. 14, the odor eliminating printed sheet 25 can be exposed as a deodorant member to the outside by cutting out and removing the covering portion 13 along the perforation 12M after use of the diaper. Accordingly, when the diaper is placed in this state into a storage container, the odor eliminating printed sheet 25 contacts directly an odor filling the storage container to perform odor elimination in a more effective manner.

Meanwhile, in the foregoing example, the perforation 12M is provided on the entire peripheral edge of the covering portion 13 so that the covering portion 13 can be entirely removed. Alternatively, the covering portion 13 may have no perforation at part of the peripheral edge thereof as a cut and remaining part, so that the covering portion 13 is not completely separated from the outer sheet 12 even when being turned up, thereby to preferably cause no small piece of waste. In this mode, when the after-treatment tape 70 is provided, the base portion of the after-treatment tape 70 is preferably fixed to the covering portion 13 near or adjacent to the perforation 12M, so that the covering portion 13 can be cut out along the perforation 12M subsequent from the removal of the after-treatment tape 70. In addition, since the covering portion 13 functions as if being part of the long after-treatment tape, there is no need to form the after-treatment tape 70 longwise unlike in a conventional manner (that is, the after-treatment tape 70 can be preferably folded in two instead of three). Accordingly, it is possible to fix the rolled or folded article and expose the deodorant member to the outside at the same time, thereby allowing easy disposal of the used article. Further, particularly in this mode, the covering portion 13 is sized and shaped so as to be almost identical to the odor eliminating printed sheet 25 or so as to cover the entire odor eliminating printed sheet 25, and the liquid impervious sheet 11 and the odor eliminating printed sheet 25 are attached to each other in a detachable manner or in such a manner that the attachment area is about 0 to 20% of the area of the odor eliminating printed sheet 25, and then the outer sheet 12 and the odor eliminating printed sheet 25 are firmly attached to each other. Accordingly, when the covering portion 13 is turned up, the odor eliminating printed sheet 25 is also turned up together with the covering portion 13, thereby enhancing an odor eliminating effect on an external odor.

The odor-eliminating printed sheet 25 as a deodorant member and the covering portion 13 desirably have larger areas for enhancement of an odor eliminating effect. However, if the covering portion 13 with a larger area is to be entirely removed as in the foregoing mode, a part for arranging the after-treatment tape 70 is decreased, which may lead to deteriorated wearability or difficulty of after-treatment of the article when the after-treatment tape 70 is located in an improper position.

Figure 17:
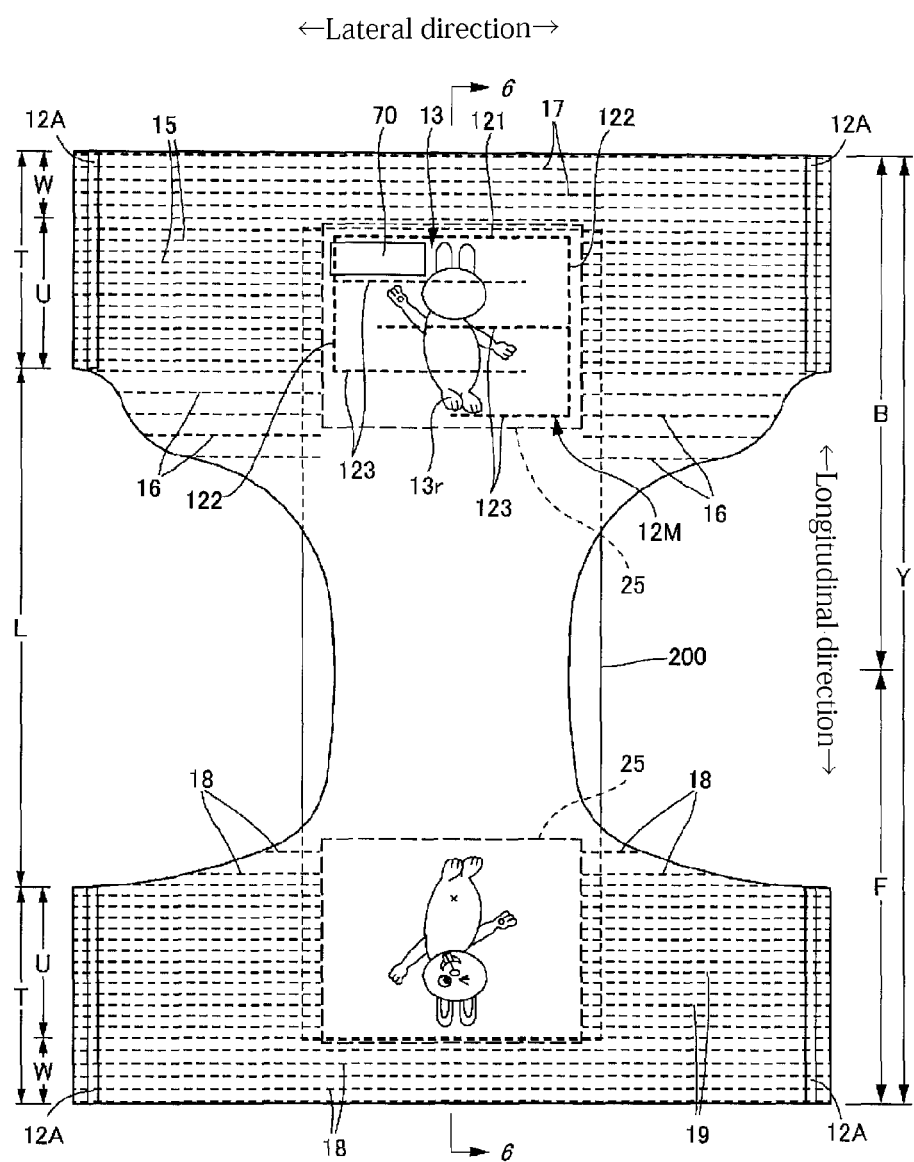
FIG. 17 is a plane view of another opened underpants type disposable diaper, showing an external surface of the diaper.
Figure 18:
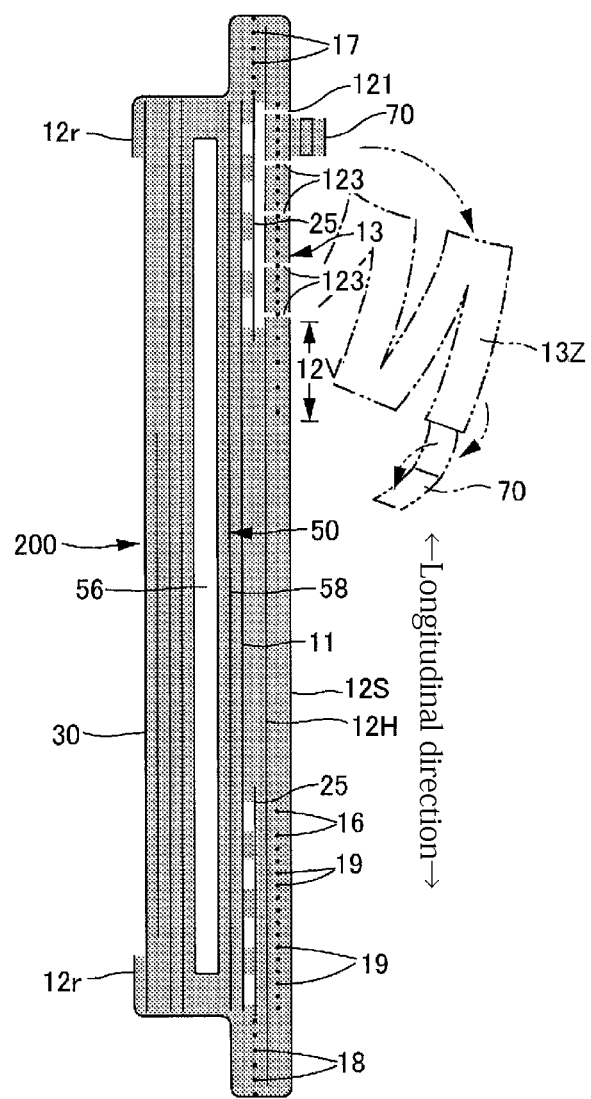
FIG. 18 is a cross-section view of FIG. 17 taken along 6-6.

Then, FIGS. 17 and 18 illustrate another mode. Specifically, in the example of the drawings, the perforation 12M is formed in such a manner that a part of the peripheral edge of the covering portion 13 is remained as a continuous part 13r from the outside and the other part of the same is cut out in a zigzag pattern, and that the after-treatment tape 70 is arranged at an end of the cut part of the covering portion 13. More specifically, the rectangular covering portion 13 has an end perforation 121 formed along an edge thereof on an opposite side of the continuous part 13r (the waist side edge in the illustrated example), and has a pair of side perforations 122 extending from the both ends of the end perforation 121 toward the continuous part (extending along the both side edges of the covering portion in the illustrated example), and has lateral perforations 123 extending from either one of the side perforations 122 toward the opposite side perforation 122, which are formed in parallel and alternately at predetermined intervals therebetween from the continuous part 13r toward the end perforation 121. The after-treatment tape 70 is arranged between the end perforation 121 and the adjacent lateral perforation 123 in parallel with these perforations.

When the covering portion 13 is cut out along the thus configured perforations 121 to 123, it is possible to not only expose the odor eliminating printed sheet 25 as a deodorant member to the outside, but also pull out the covering portion 13 to form along zigzag portion 13Z from the outer sheet 12 and wind the long portion 13Z around the rolled or folded article after use, and then extend and fasten the after-treatment tape 70 with an adhesive surface to the external surface of the rolled or folded article, thereby fixing the article after use.

Although the zigzag long portion 13Z is formed in the illustrated example, a spiral long portion may be formed instead in another perforation pattern.

Figure 19:
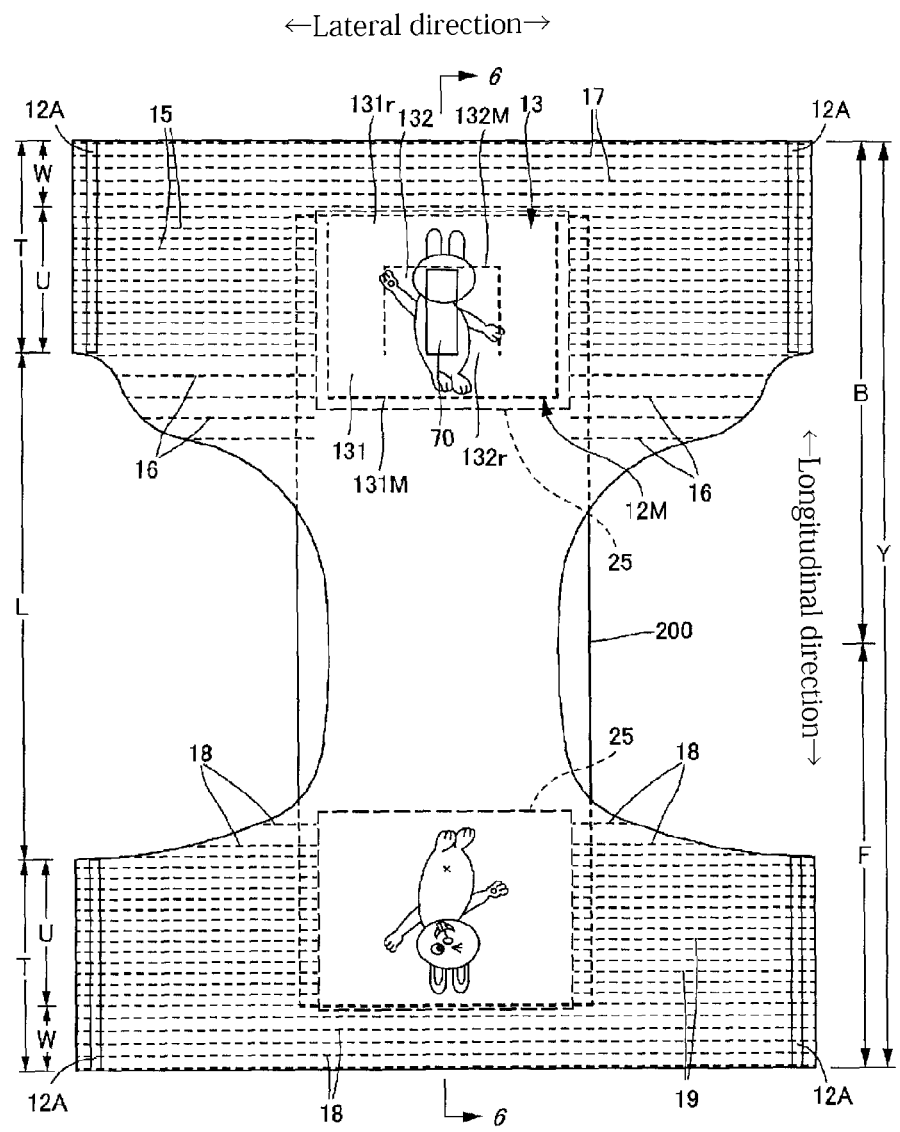
FIG. 19 is a plane view of another opened underpants type disposable diaper, showing an external surface of the diaper.
Figure 20:
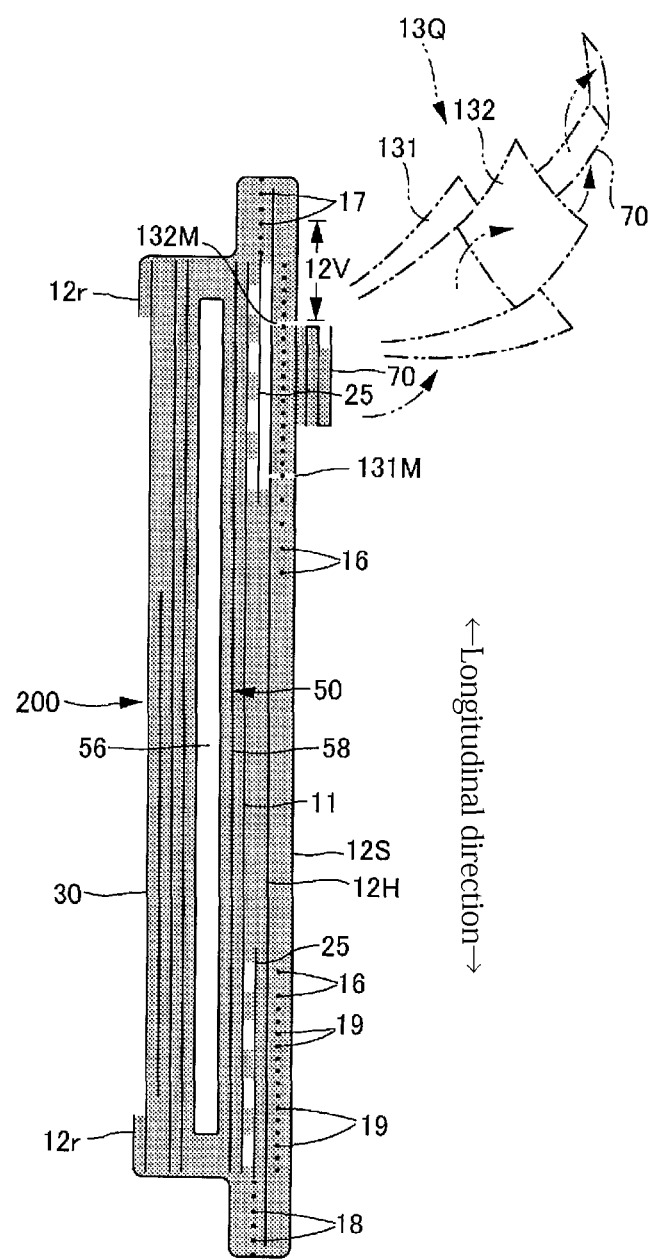
FIG. 20 is a cross-section view of FIG. 19 taken along 6-6.

In addition, FIGS. 19 and 20 illustrate a mode for enabling more stable fixation. Specifically, in the example of these drawings, the perforation 12M includes a first perforation 131M formed in the shape of an approximate U letter such that a waist side end of the peripheral edge of the covering portion 13 is remained as a continuous part 131r from a waist side part, and that the other part is cut and raised as a first cut and rise part 131; and a second perforation 132M formed in the shape of an approximately reversed U letter such that, within the first cut and rise part 131, a crotch side end of the covering portion 13 is remained as a continuous part 132r from a crotch side part, and that a waist side part of the first cut and rise part 131 is cut and raised as a second cut and rise part 132. In addition, the after-treatment tape 70 is arranged at the second cut and rise part 132.

In this case, when the covering portion is partly cut out along the first and second perforations 131M and 132M and then the first and second cut and rise parts 131 and 132 are turned up and raised as shown by chain double-dashed lines in FIG. 20, it is possible to not only expose the odor eliminating printed sheet 25 as a deodorant member to the outside, but also wind a long part 13Q constituted by the first cut and rise part 131 extending from the outer sheet 12 and the second cut and rise part 132 extending from the first cut and rise part 131 around the rolled or folded article after use, and then extend and fasten the after-treatment tape 70 with an adhesive surface to the external surface of the rolled or folded article for fixation of the article.

In the examples shown in FIGS. 17 to 20, it is possible to fix the rolled or folded article for disposal without any long after-treatment tape as in the conventional manner, and at the same time, it is possible to expose the deodorant member to the outside, thereby allowing easier disposal of the used article. Therefore, instead of the folding-type after-treatment tape 70 as in the illustrated example, any other fixing means for the external surface of the article, for example, a hook tape of a mechanical fastener (hook and loop fastener) or a pressure-sensitive adhesive may be directly arranged at a tip portion of the long part. In the case of arranging such a hook tape or a pressure-sensitive adhesive directly at the tip portion of the long part, the tape or the adhesive may be located on the external surface side or the odor eliminating printed sheet 25 side of the outer sheet 12. In addition, the continuous part formed by cutting the article along the perforations constitutes a base part connecting the after-treatment tape 70 and the outer sheet 12, and the base part may be subjected to a strong force when the rolled or folded article is fixed after use. Accordingly, it is preferred that, in an area 12V of the outer sheet 12 including the continuous part formed by cutting along the perforation and a neighboring part of the continuous part, an inner layer 12H and an outer layer 12S are attached to each other more firmly than at surroundings of the area 12V. Accordingly, it is preferred to increase locally an application amount of the adhesive, and alternatively, it is possible to use another kind of an adhesive for the attachment.

Figure 21:
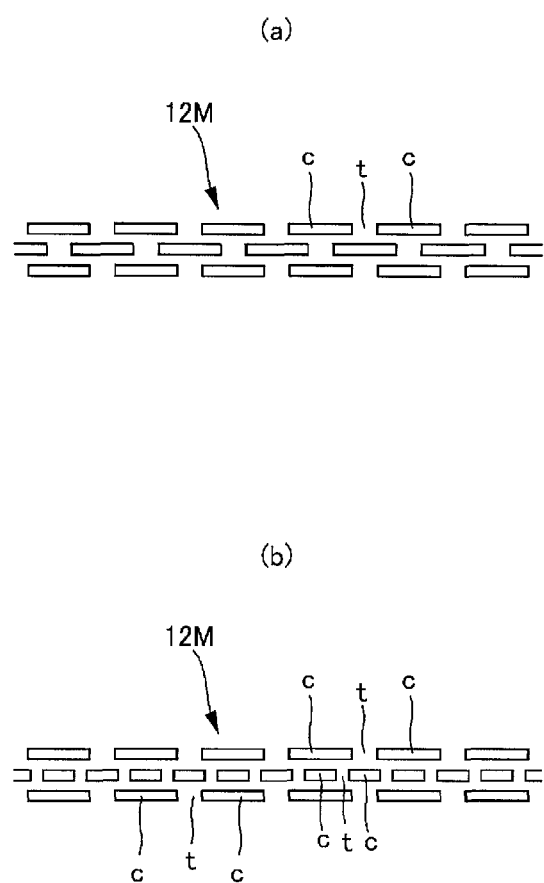
FIG. 21 is an enlarged plane view of perforations.

Meanwhile, the outer sheet 12 constitutes the external surface of the article, and therefore preferably uses a relatively high-strength material such as a spun bond nonwoven fabric. However, if such a high-strength material is used and the perforation 12M is formed in a single-line pattern, the outer sheet 12 may be difficult to cut out. Accordingly, as shown in FIG. 21, it is preferred to form a plurality of perforations in parallel in a double-line or triple-line pattern such that adjacent perforations 12M have cuts c and ties t shifted in position from each other. In this case, it is preferred to make a cut pitch of the perforation 12M on the outermost side (farthest from the center of the covering portion 13) longer than that of the perforation 12M on the innermost side (nearest to the center of the covering portion 13).

In addition, if the foregoing cutting mode of the resilient and elastic members 15, 16, 18, and 19 is employed, that is, if the resilient and elastic members are arranged across the inner body 200 from one side to the other side in the lateral direction but the resilient and elastic members are cut in the central portion of the outer sheet 12 overlapping the inner body 200 in the lateral direction so as not to exert no contraction force (which is virtually equal to not providing the resilient and elastic members), the foregoing perforation 12M in particular extending in the longitudinal direction may be processed in such a manner as to cut some or all of the elongated resilient and elastic members 15, 16, 18, and 19 using the cuts of the perforations.

(Outer Sheet Separation Structure)

In the foregoing example, the unified outer sheet 12 covers the front body part F and the back body part B in a continuous manner. As an alternative arrangement, the outer sheet may be separated into a ventral side outer sheet covering the ventral side of the trunk of a wearer and a back side outer sheet covering the back side of the trunk of the wearer. In this arrangement, the front end of the inner body is connected with a hot-melt adhesive or the like to an internal surface of a central portion of the ventral side outer sheet in the lateral direction, and a back end of the inner body is connected with a hot-melt adhesive or the like to the internal surface of the central portion of the back side outer sheet in the lateral direction, and the ventral side outer sheet and the back side outer sheet are not connected but separated from each other at the crotch portion. A distance of the separation may be about 150 to 250 mm. In this case, a crotch outer sheet may be fixed to the back surface of the liquid impervious sheet in the inner body so as to cover the entire back surface of the inner body or cover an entire part exposed between the ventral side outer sheet and the back side outer sheet. The crotch outer sheet may use the same material as that for the foregoing outer sheet. The crotch outer sheet is also equivalent to the outer sheet of the present invention.

EXAMPLES

The inventors carried out several experiments according to the following steps (1) to (4) for testing an odor eliminating effect on odor substances (methyl mercaptan and hydrogen sulfide) with different kinds (particle diameters) of deodorant agents and different application amounts of the same. Used detector tubes are produced by Gastec Corporation (No. 70L for methyl mercaptan and No. 4LT or 4LK for hydrogen sulfide). The ambient temperature for the experiments was 20° C. Unless otherwise specified, all the experiments were carried out under the same conditions.

(1) Cut a sheet-like sample into a piece of 180 mm×90 mm.

(2) Place the sample into a 5 L experiment bag (Tedlar bag for odor measurement) and inject an air of 3 L into the bag.

(3) Inject an experimental gas (methyl mercaptan and hydrogen sulfide) into the experimental bag of step (2) in a concentration of 4 ppm (initial concentration).

(4) After each lapse of a specific period of time (2, 4, and 6 hours), measure a concentration of residual gas with the detector tube.

Table 1 shows experimental results. Blanks in Table 1 refer to odor eliminating printed sheets with no deodorant particle. As shown in the table, the experiments have revealed that the samples containing the deodorant particles with average particle diameters of 2.0 μm or more were higher in deodorant performance. In addition, the experiments have shown that silicate and zeolite with larger surface areas and larger physical absorptive capacity achieved higher deodorant performance than zinc oxide with smaller physical absorptive capacity. Further, the experiments have demonstrated that the deodorant particle with an average particle diameter of 2.0μ or more exerted an odor eliminating effect by an application amount of 5 parts by weight or more (ratio by weight with respect to 100 parts by weight of adhesive resin).

TABLE 1

| | | | Experimental gas | | | | | | | | | | | |
|---|---|---|---|---|---|---|---|---|---|---|---|---|---|---|
| | | | Methyl mercaptan | | | | | | Hydrogen sulfide | | | | | |
| | | | Initial concentration | | | | | | | | | | | |
| | | | 4 ppm/3 L | | | | | | 4 ppm/3 L | | | | | |
| Deodorant | | | 2 h | | 6 h | | 24 h | | 2 h | | 6 h | | 24 h | |
| Kind | Composition | Particle diameter | Concentration ppm | Decrease ratio % | Concentration ppm | Decrease ratio % | Concentration ppm | Decrease ratio % | Concentration ppm | Decrease ratio % | Concentration ppm | Decrease ratio % | Concentration ppm | Decrease ratio % |
| Deodorant A Application | Copper + zirconium phosphate | 0.8 | 4.0 | 0% | 4.0 | 0% | 4.0 | 0% | 4.0 | 0% | 4.0 | 0% | 3.6 | 10% |
| Deodorant A Application | | | 4.0 | 0% | 4.0 | 0% | 4.0 | 0% | 3.4 | 15% | 3.4 | 15% | 3.4 | 15% |
| Deodorant B Application | Copper + silicate | 4.9 | 3.5 | 13% | 3.5 | 13% | 2.5 | 38% | 2.8 | 30% | 2.0 | 50% | 0.0 | 100% |
| Deodorant B Application | | | 3.0 | 25% | 2.5 | 38% | 0.5 | 88% | 1.6 | 60% | 0.4 | 90% | 0.0 | 100% |

TABLE 1-continued

| | | | Experimental gas | | | | | | | | | | |
|---|---|---|---|---|---|---|---|---|---|---|---|---|---|
| | | | Methyl mercaptan | | | | | | Hydrogen sulfide | | | | |
| | | | Initial concentration | | | | | | | | | | |
| | | | 4 ppm/3 L | | | | | | 4 ppm/3 L | | | | | |
| Deodorant | | | 2 h | | 6 h | | 24 h | | 2 h | | 6 h | | 24 h | |
| Kind | Composition | Particle diameter | Concentration ppm | Decrease ratio % | Concentration ppm | Decrease ratio % | Concentration ppm | Decrease ratio % | Concentration ppm | Decrease ratio % | Concentration ppm | Decrease ratio % | Concentration ppm | Decrease ratio % |
| Deodorant B Application | | | 1.5 | 63% | 0.0 | 100% | 0.0 | 100% | 0.0 | 100% | 0.0 | 100% | 0.0 | 100% |
| Deodorant C Application | Zinc oxide | 10 | 3.8 | 5% | 3.8 | 5% | 3.8 | 5% | 2.8 | 30% | 2.0 | 50% | 0.4 | 90% |
| Deodorant C Application | | | 3.5 | 13% | 3.5 | 13% | 3.2 | 20% | 1.3 | 68% | 0.5 | 88% | 0.4 | 90% |

INDUSTRIAL APPLICABILITY

The present invention is suited for underpants type disposable diapers as in the foregoing examples, and can also be applied to tape type disposable diapers.

BRIEF DESCRIPTION OF NUMERALS

11 . . . Liquid impervious sheet, 12 . . . Outer sheet, 12M . . . Perforation, 12r . . . Turndown portion, 25 . . . Odor eliminating printed sheet, 200 . . . Inner body, 30 . . . Top sheet, 40 . . . Interlayer sheet, 50 . . . Absorbent element, 56 . . . Absorbent body, 58 . . . Package sheet, 60 . . . Side barrier cuff, 62 . . . Barrier sheet.

The invention claimed is:

1. A disposable diaper, comprising a liquid pervious face sheet, a liquid impervious sheet having an internally facing side and an externally facing side, an absorbent body interposed between the two sheets, and an odor eliminating printed sheet arranged on the externally-facing side of the liquid impervious sheet,
the disposable diaper having a back body part extending backward from a center of the diaper in a longitudinal direction, a front body part extending frontward from the center of the diaper in the longitudinal direction, and an after-treatment tape on an external surface of at least one of the front body part and the back body part to fix the diaper in a state of being rolled or folded with the face sheet positioned inside, wherein
the odor eliminating printed sheet is arranged on at least one of the front body part and the back body part whichever has the after-treatment tape, and is smaller in area than the body part on which the same is arranged, and at least part of the same overlaps the absorbent body;
the after-treatment tape has a base portion fixed to the external surface of the diaper and an engage portion that is positioned nearer to a tip portion than the base portion and is engaged on the external surface of the diaper, and
the after-treatment tape is arranged in such a manner that at least part of the base portion overlaps the odor eliminating printed sheet in the body part on which the same is arranged.

2. The disposable diaper according to claim 1, wherein
the odor eliminating printed sheet is provided with a design print, and the design print can be seen from an external surface side of the diaper.

3. The disposable diaper according to claim 2, wherein
the odor eliminating printed sheet is an air permeable sheet containing nonwoven fabric or paper as base materials, and
the odor eliminating printed sheet is arranged on both the front body part and the back body part, and the after-treatment tape is arranged on at least one of the front body part and the back body part.

4. The disposable diaper according to claim 1, wherein
the odor eliminating printed sheet has an area of 30% or more of an area of the absorbent body in the body part on which the same is arranged, and overlaps the absorbent body by 80% or more of the area, and
the liquid impervious sheet has a moisture permeability of 6,000 g/m$^2$·24 h or more.

5. The disposable diaper according to claim 4, wherein the after-treatment tape has a tab part at a tip portion thereof and has a transparent or translucent part other than the tab part, and the printed design can be seen from the external surface side through the transparent or translucent remaining part of the after-treatment tape.

6. The disposable diaper according to claim 5, comprising an outer sheet made from nonwoven fabric to cover a back surface of the liquid impervious sheet, the odor eliminating printed sheet being interposed between the liquid impervious sheet and the outer sheet, wherein
the odor eliminating printed sheet and the liquid impervious sheet are stuck to each other by an attachment area of 70% or less of an area of the odor eliminating printed sheet, and
the odor eliminating printed sheet and the outer sheet are stuck to each other by an attachment area of 80% or more of the area of the odor eliminating printed sheet.

7. The disposable diaper according to claim 1, wherein
the after-treatment tape is arranged on a left side of a left edge of the absorbent body and on a right side of a right edge of the same, and the odor eliminating printed sheet is arranged in such a manner that a line linking the right and left after-treatment tapes straddles the odor eliminating printed sheet.

8. The disposable diaper according to claim 1, wherein the odor eliminating printed sheet has a sheet base material and a deodorant particle fixed to the sheet base material with an adhesive resin, and part of the deodorant particle on an outer surface is not covered with the adhesive resin.

9. The disposable diaper according to claim 8, wherein the deodorant particle has an average particle diameter of 2.0 to 8.0 μm, the deodorant particle accounts for 50 to 100 parts by weight with respect to 100 parts by weight of the adhesive resin, and a total content of the deodorant particle and the adhesive resin is 0.10 to 0.60 g per 1 $m^2$ of the odor eliminating printed sheet.

10. The disposable diaper according to claim 9, wherein the adhesive resin is a urethane-based resin.

11. The disposable diaper according to claim 10, wherein the deodorant particle has a three-dimensional structure, a layered structure, or a porous structure, for physical absorption of an odor, and contains a metal ion for chemical absorption of an odor molecule.

12. The disposable diaper according to claim 1, wherein a porous deodorant particle absorbing physically an odor is attached with ink as an attachment means to the sheet base material of the odor eliminating printed sheet.

13. The disposable diaper according to claim 12, wherein the deodorant particle has an average particle diameter of 0.1 to 10 μm, and the odor eliminating printed sheet has a content of the deodorant particle of 0.01 $g/m^2$ or more per unit area in a part including the deodorant particle.

14. The disposable diaper according to claim 13, comprising an outersheet made from nonwoven fabric to cover a back surface of the liquid impervious sheet, wherein
the sheet base material is provided with a deodorant print with ink containing the porous deodorant particle on the liquid impervious sheet side thereof, and the sheet base material is provided with a design print on the outer sheet side thereof.

15. The disposable diaper according to claim 14, wherein the odor eliminating printed sheet is attached intermittently to the liquid impervious sheet, and an attachment area of the same is 70% or less of an area of the odor eliminating printed sheet.

16. The disposable diaper according to claim 12, wherein the deodorant particle is a zeolite particle formed by substituting some or all of an ion-exchangeable ion in zeolite with silver ion, and at least one of the following arrangements (a) to (c) is employed:
(a) a content of silver ion per unit area of the odor eliminating printed sheet is 0.3 $mg/m^2$;
(b) yellow ink is used as the attachment means; and
(c) the sheet base material has a total light transmission rate of 50% or less defined by JIS K7105, and has the porous deodorant particle attached only to the liquid impervious sheet side thereof.

17. The disposable diaper according to claim 1, comprising an outer sheet made from nonwoven fabric to cover a back surface of the liquid impervious sheet, wherein
the outer sheet is provided with a perforation on an entire or partial peripheral edge of a covering portion overlapping at least part of a portion of the odor eliminating printed sheet with an odor eliminating function, and the odor eliminating printed sheet is exposed to the outside by cutting out the outer sheet along the perforation and turning up the covering portion.

18. The disposable diaper according to claim 17, wherein the perforation is formed in such a manner that a partial peripheral edge of the covering portion is remained as a continuous part from the outside and the other part of the covering portion is cut out in a zigzag or spiral pattern, and the after-treatment tape is arranged at a tip portion of the cutting part.

19. The disposable diaper according to claim 17, wherein the perforation includes a first perforation formed in such a manner that a waist side end of the peripheral edge of the covering portion is remained as a continuous part from a waist side part of the same and that the other part of the covering portion is cut and raised as a first cut and rise part; and a second perforation formed in such a manner that a crotch side end of the covering portion within the first cut and rise part is remained as a continuous part from a crotch side part of the same and that a waist side part of the first cut and rise part is cut and raised as a second cut and rise part, and
the after-treatment tape is arranged at the second cut and rise part.

* * * * *